(12) United States Patent
Sharifi-Mehr et al.

(10) Patent No.: US 11,589,941 B2
(45) Date of Patent: Feb. 28, 2023

(54) PEDICLE SUBTRACTION OSTEOTOMY GUIDE

(71) Applicant: Stryker European Operations Holdings LLC, Kalamazoo, MI (US)

(72) Inventors: Amir Ali Sharifi-Mehr, Bloomingdale, NJ (US); Oliver Buchert, Franklin Lakes, NJ (US); Bryan Weiner, Randolph, NJ (US); M. Todd Miller, Franklin Lakes, NJ (US); Steven F. Krause, Oakland, NJ (US); Michael Chang, Phoenix, AZ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 216 days.

(21) Appl. No.: 17/036,733

(22) Filed: Sep. 29, 2020

(65) Prior Publication Data
US 2021/0015502 A1   Jan. 21, 2021

Related U.S. Application Data

(63) Continuation of application No. 16/152,621, filed on Oct. 5, 2018, now Pat. No. 10,820,917.
(Continued)

(51) Int. Cl.
*A61B 17/17* (2006.01)
*A61B 34/30* (2016.01)
*A61B 34/00* (2016.01)
*A61B 17/16* (2006.01)
*A61B 90/50* (2016.01)
(Continued)

(52) U.S. Cl.
CPC .......... *A61B 34/76* (2016.02); *A61B 17/151* (2013.01); *A61B 17/1604* (2013.01); *A61B 17/1757* (2013.01); *A61B 34/30* (2016.02); *A61B 90/50* (2016.02); *A61B 17/152* (2013.01);
(Continued)

(58) Field of Classification Search
CPC ............................ A61B 17/1757; A61B 34/76
See application file for complete search history.

(56) References Cited

U.S. PATENT DOCUMENTS 4,421,112 A * 12/1983 Mains ................ A61B 17/1764
606/88
5,722,978 A   3/1998 Jenkins, Jr.
(Continued)

FOREIGN PATENT DOCUMENTS

CA     3001898 A1    4/2017

OTHER PUBLICATIONS

Extended European Search Report and Written Opinion for EP Application No. 18198745.4, dated Mar. 6, 2019.

*Primary Examiner* — Christian A Sevilla
(74) *Attorney, Agent, or Firm* — Lerner, David, Littenberg, Krumholz & Mentlik, LLP

(57) ABSTRACT

A virtual surgical cutting guide may have first and second slots defining first and second axes respectively. The virtual surgical cutting guide may be positioned away from a vertebral body such that the first and second axes intersect at a distal point located in an interior of the vertebral body. The virtual surgical cutting guide may include the virtual surgical cutting guide with first and second cutting instruments. A method of performing a pedicle subtraction osteotomy may include the steps of placing the virtual surgical cutting guide over the first and second cutting instruments.

20 Claims, 23 Drawing Sheets

Related U.S. Application Data

(60) Provisional application No. 62/569,035, filed on Oct. 6, 2017.

(51) Int. Cl.
*A61B 17/15* (2006.01)
*A61B 90/00* (2016.01)

(52) U.S. Cl.
CPC ..... *A61B 17/1671* (2013.01); *A61B 2090/034* (2016.02); *A61B 2090/3966* (2016.02)

(56) References Cited

U.S. PATENT DOCUMENTS

| | | | |
|---|---|---|---|
| 5,980,526 A | 11/1999 | Johnson et al. | |
| 6,642,686 B1 * | 11/2003 | Ruch | A61B 34/76 318/568.14 |
| 7,206,626 B2 * | 4/2007 | Quaid, III | A61B 17/1703 600/407 |
| 8,828,087 B2 | 9/2014 | Stone et al. | |
| 9,198,671 B2 | 12/2015 | Jacobs | |
| 2004/0034283 A1 * | 2/2004 | Quaid, III | A61B 34/32 600/300 |
| 2011/0112542 A1 * | 5/2011 | Gross | A61F 2/4684 606/88 |
| 2013/0123786 A1 | 5/2013 | McCormack | |
| 2016/0095634 A1 | 4/2016 | Meyer | |
| 2017/0135706 A1 * | 5/2017 | Frey | A61B 17/1671 |

\* cited by examiner

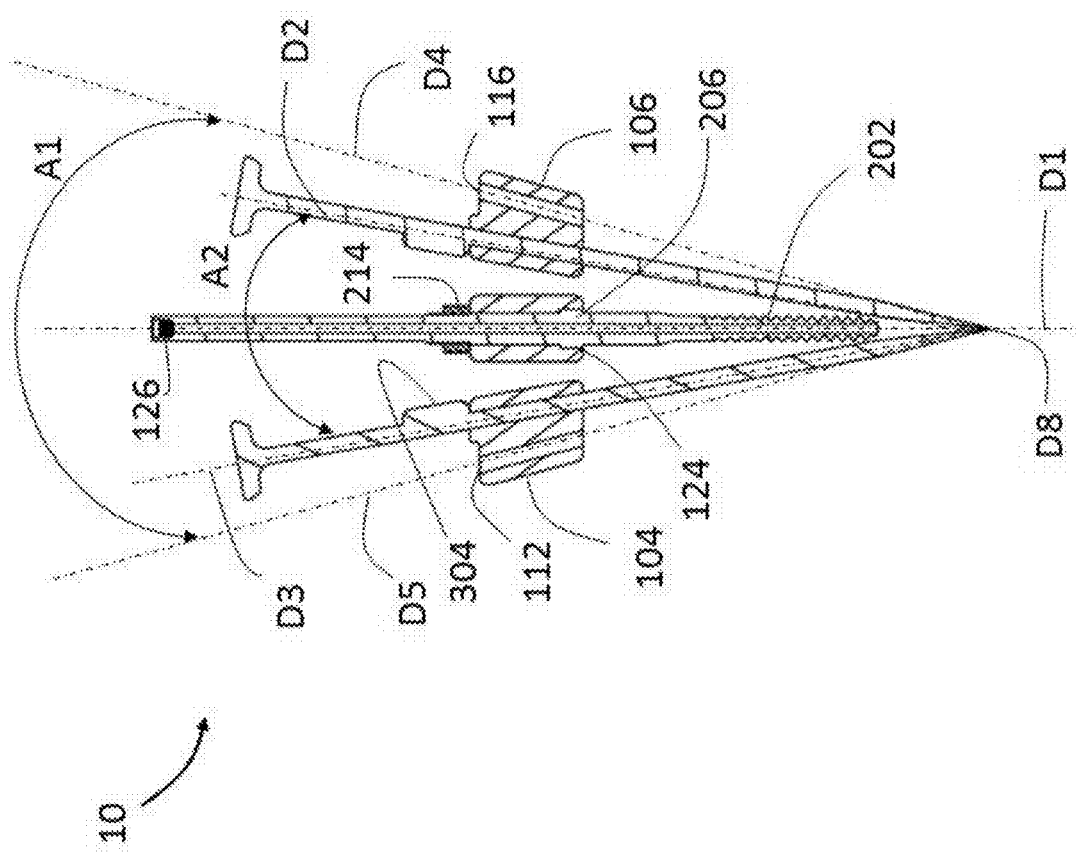

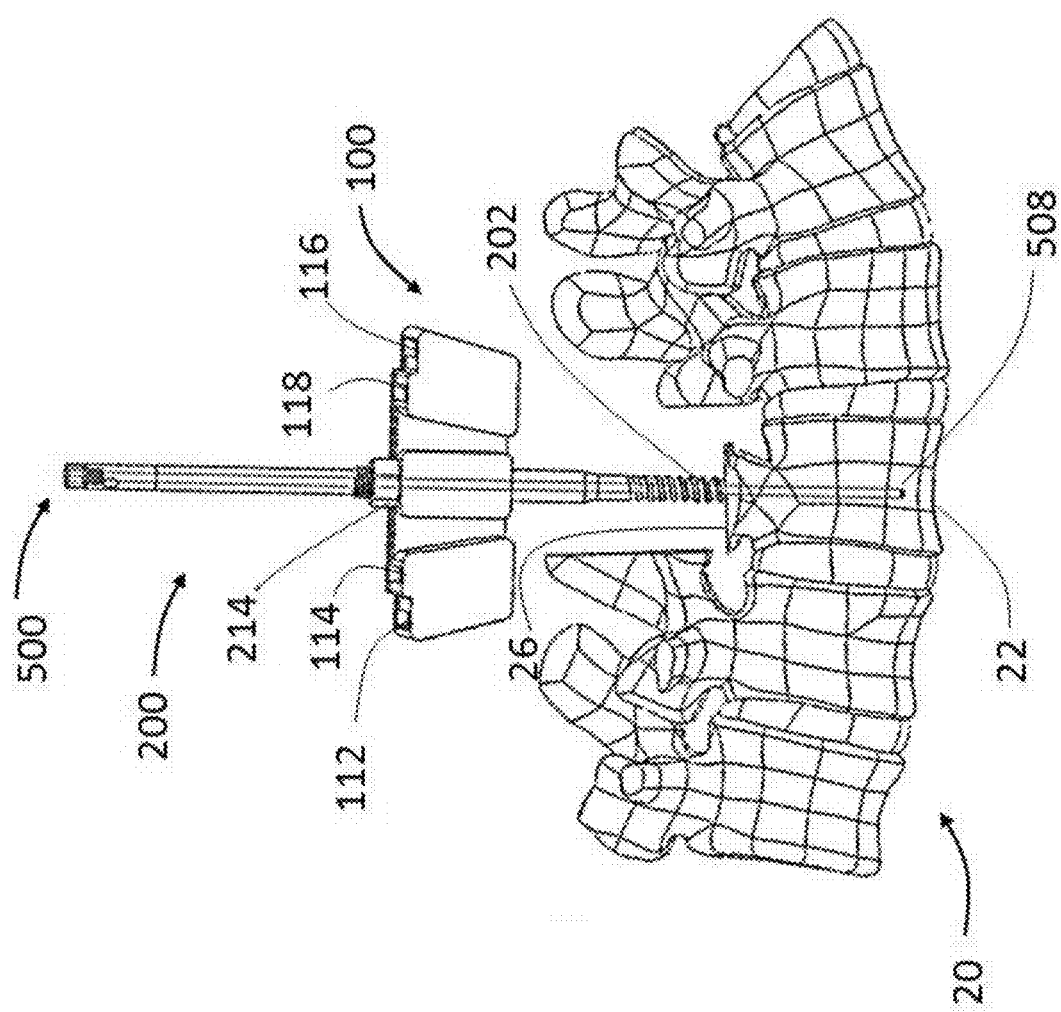

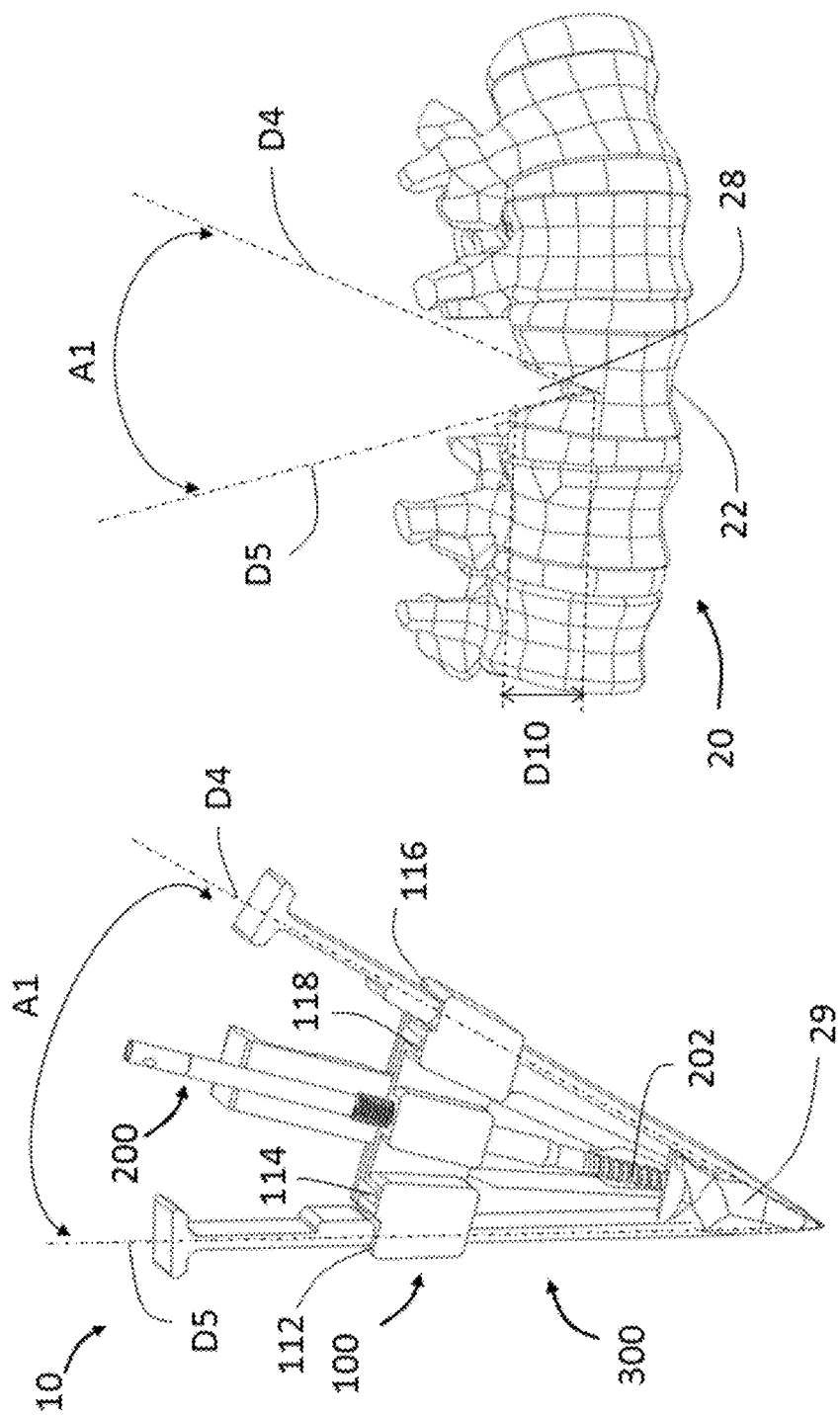

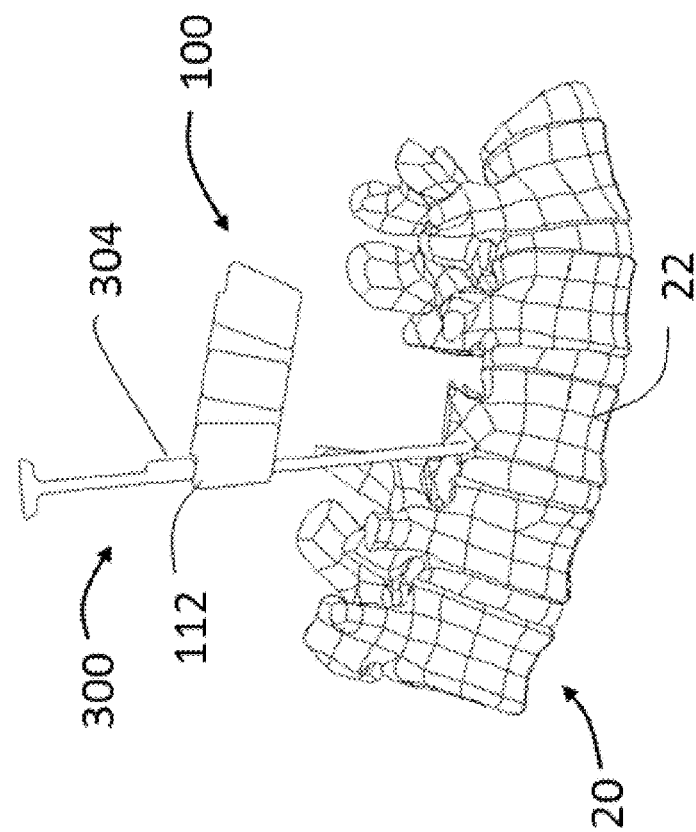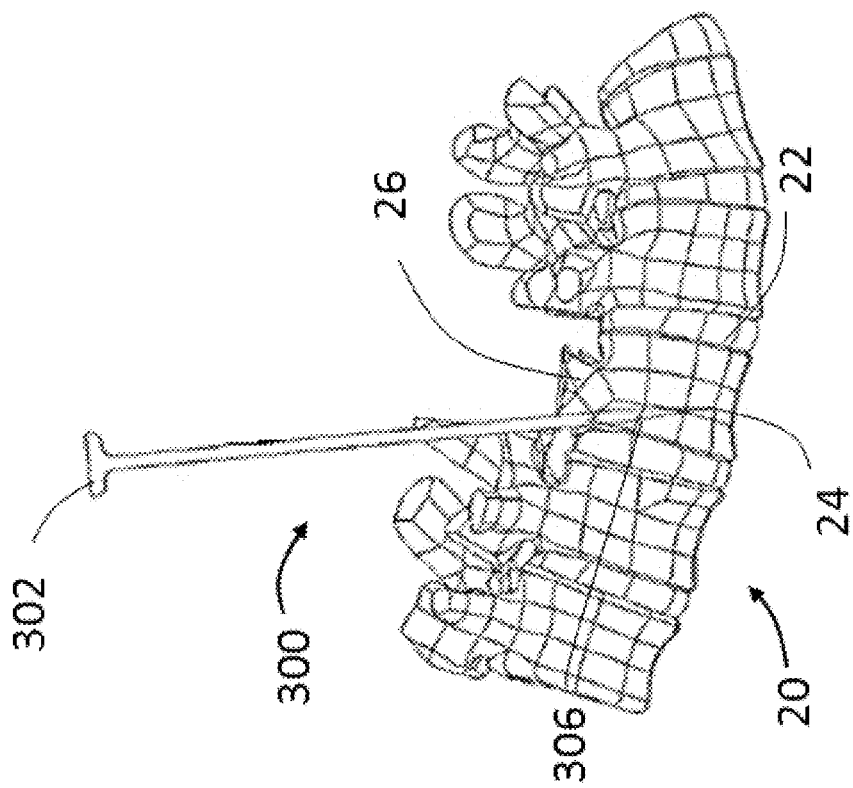
FIG. 13A
FIG. 13B

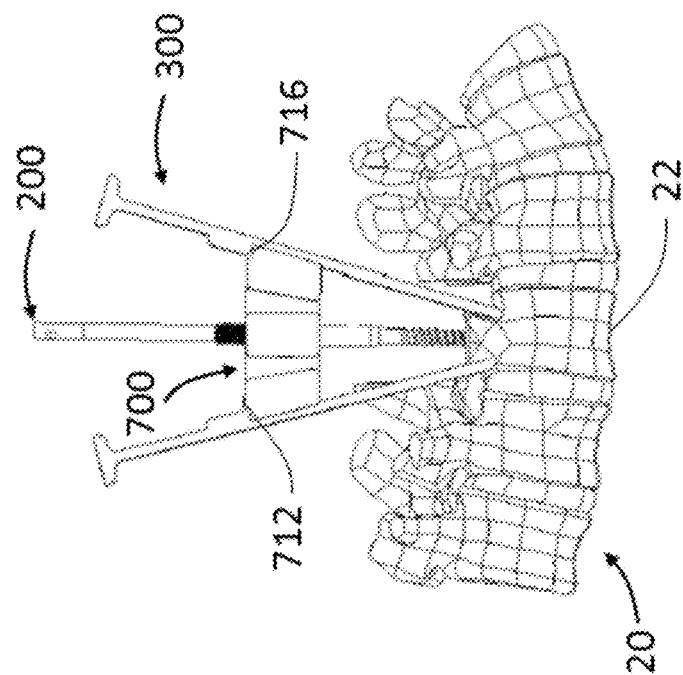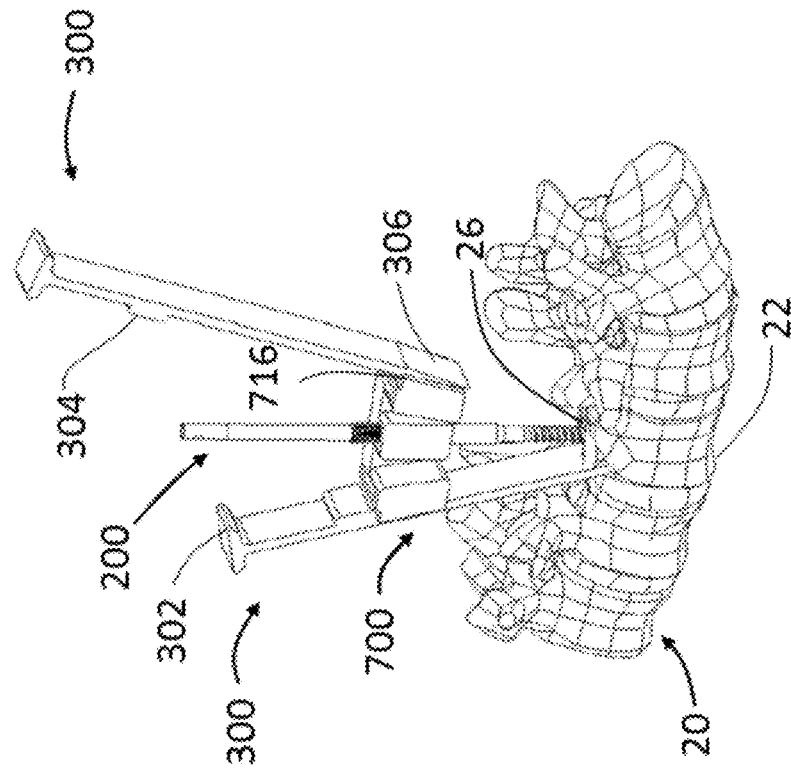

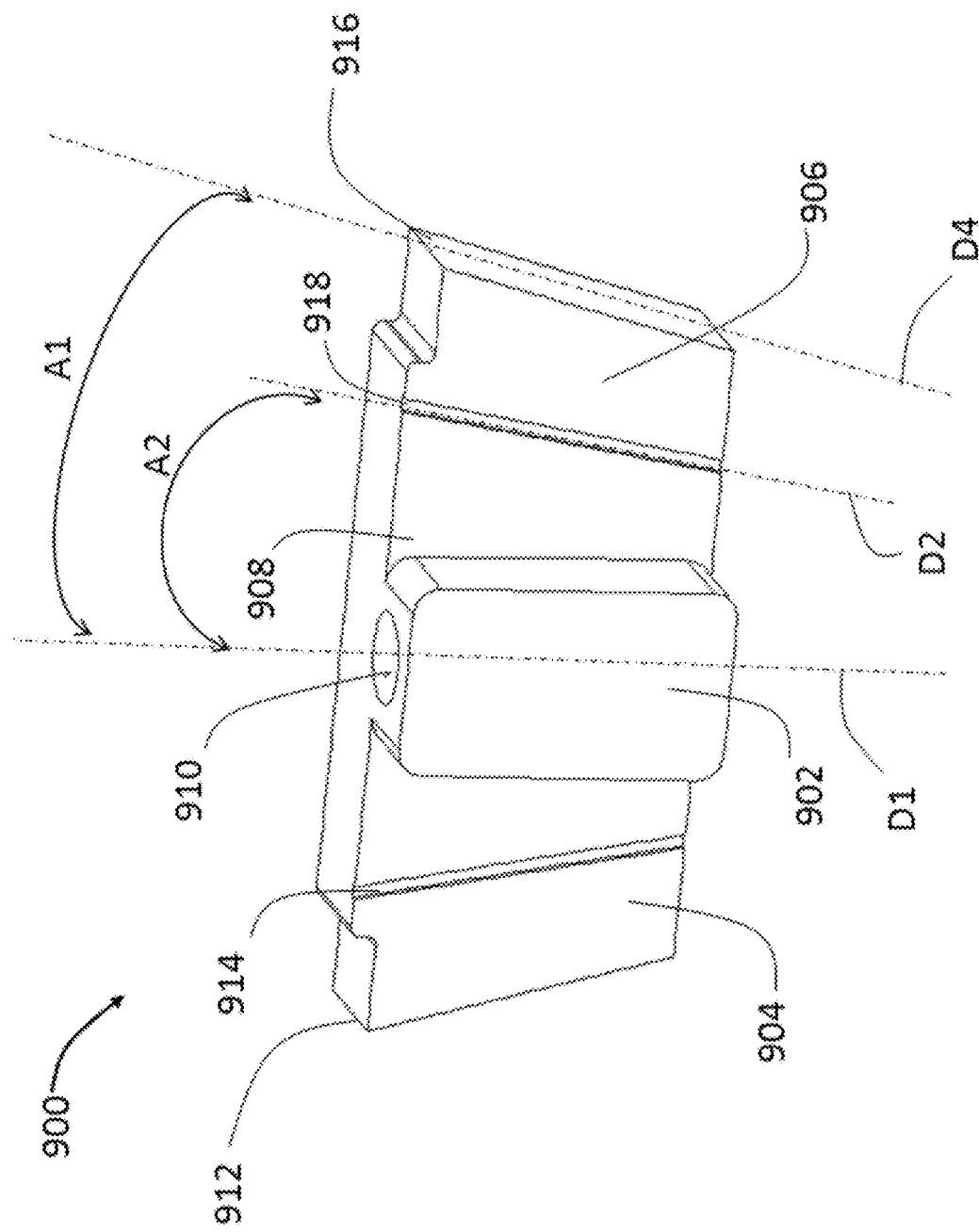

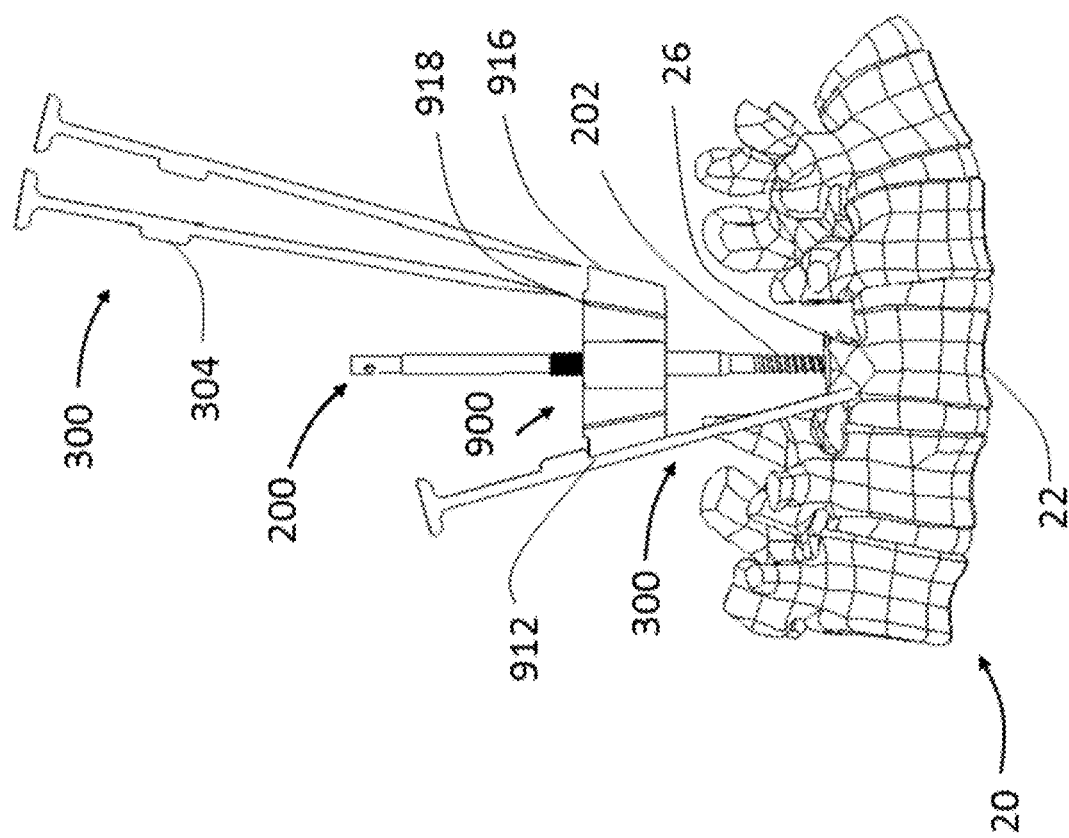

PEDICLE SUBTRACTION OSTEOTOMY GUIDE

CROSS-REFERENCE TO RELATED APPLICATION

The present application is a continuation of U.S. patent application Ser. No. 16/152,621 filed Oct. 5, 2018, which claims the benefit of the filing date of U.S. Provisional Patent Application No. 62/569,035, filed on Oct. 6, 2017, the disclosures of which are hereby incorporated herein by reference.

FIELD OF THE INVENTION

The present invention generally relates to a cutting guide assembly and a method for using the same, and in particular, relates to a pedicle subtraction osteotomy guide assembly and a method for using same.

BACKGROUND OF THE INVENTION

A pedicle subtraction osteotomy ("PSO") is one type of procedure performed to correct spinal deformities caused by improper spinal alignment. For instance, conditions such as scoliosis, hyperkyphosis, and ankylosing spondylitis are known to cause spinal misalignment. A misaligned spine may prevent pain-free functioning of the spine.

A PSO is performed by removing a moderate amount of vertebral bone to realign a vertebral body and may be conducted with other forms of osteotomies such as other posterior column osteotomies or vertebral column resection to treat a specific spinal deformity. Facet joints at the back of the vertebra, pedicles that attach the back of the vertebra, the laminae and a portion of the vertebral body are typically removed in a PSO. Subtraction angles indicate the degrees of spinal alignment correction that may be achieved (typically from 15 to 35 degrees).

A surgeon generally performs a PSO with chisels, osteotomes, box cutters and mallets. These tools are generally used freehand, without the aid of any guiding instruments. Consequently, precise control of surgical equipment to obtain the desired subtraction angles may not be achieved. Furthermore, the use of impaction equipment such as mallet and slap hammers to distally advance the cutting instruments into vertebral body may result in improper trajectory of these instruments which can lead to an unsuccessful PSO or may even risk injury to the patient.

Therefore, there exists a need for an improved cutting guide with greater cutting accuracy and a cutting guide assembly.

BRIEF SUMMARY OF THE INVENTION

Disclosed herein are surgical cutting guides and methods of performing pedicle subtraction osteotomy procedures using same.

In a first aspect according to the present invention, a surgical cutting guide for a spinal procedure is provided. The surgical cutting guide according to the first aspect may include a first slot and a second slot. The first slot may extend from a proximal face to a distal face, and may have a first axis extending therethrough defining a first channel to receive a first cutting instrument. The second slot may extend from the proximal face to the distal face. The second slot may have a second axis therethrough. The second slot may be located opposite the first slot and may define a second channel to receive a second cutting instrument. The cutting guide may be positioned away from a vertebral body such that the when the distal face faces the vertebral body, the first and second channels may be oriented such that the first and second axes may extend distally towards each other and intersect at a distal point located in an interior of the vertebral body.

In accordance with the first aspect, a cross-section of the first slot may be substantially the same as a cross-section of the first cutting instrument and a cross-section of the second slot may be substantially the same as a cross-section of the second cutting instrument such that the first and second slots may guide the first and second cutting instruments respectively. The first slot and the second slot may have at least one or more similarly oriented slots respectively.

The surgical cutting guide according to this first aspect may include a third slot extending from the proximal to the distal face of the cutting guide having a third axis extending therethrough and intersecting with the first and second axes at the distal point. The third slot may define a third channel to receive a post, a cross-section of the third slot may be substantially the same as a cross-section of the post. A distal end of the third slot may include a counter bore to receive a distal nut of the post. The surgical cutting guide may include a fourth slot extending from the proximal face to the distal face of the cutting guide. The fourth slot may be located between the first and second slots. The fourth slot may be substantially transverse to the first and second slots and may define a fourth channel to receive a third cutting instrument. A cross-section of the fourth slot may be substantially the same as a cross-section of the third cutting instrument to guide the third cutting instrument.

Still further in accordance with the first aspect, a superior face of the cutting guide may be parallel to the first channel and an inferior face of the cutting guide may be parallel to the second channel. The superior face may have peripheral ridges on medial and lateral edges to guide the first cutting tool. The inferior face may have peripheral ridges on medial and lateral edges to guide the second cutting tool. The intersection of the first and second axes may define a subtraction angle for a pedicle subtraction osteotomy.

In accordance with a second aspect of the present invention, a surgical cutting guide is provided. The surgical cutting guide of the second aspect may include a superior face and an inferior face extending from a distal face to a proximal face of the cutting guide. The superior face may be capable of engaging and guiding a first cutting instrument in a first plane. The inferior face may be capable of engaging and guiding a second cutting instrument in a second plane. The first and second plane may extend distally towards each other and intersect distally to the cutting guide.

In accordance with the second aspect of the present invention, the cutting guide may include a first groove extending from the distal face to the proximal face of the cutting guide and parallel to the superior face. The first groove may be able to receive and guide a first cutting instrument. A second groove may extend from the distal face to the proximal face of the cutting guide and parallel to the inferior face. The second groove may be able to receive and guide a second cutting instrument.

In accordance with a third aspect of the present invention, a surgical cutting guide is provided. A surgical cutting guide according to the third aspect may include a superior face and an inferior face extending from a distal face to a proximal face of the cutting guide. The superior face may be capable of engaging and guiding a first cutting instrument in a first plane. The inferior face may be capable of engaging and guiding a second cutting instrument in a second plane. The first and second plane may extend distally away from the cutting guide and towards each other to intersect distally to the cutting guide.

In accordance with a fourth aspect of the present invention, a surgical cutting guide assembly is provided. A surgical cutting guide assembly according to the fourth aspect may include a cutting guide, a first cutting instrument and a second cutting instrument. The cutting guide may have a first slot extending from a proximal face to a distal face having a first axis extending therethrough. The first slot may define a first channel A second slot may extend from the proximal face to the distal face having a second axis therethrough. The second slot may be located opposite the first slot defining a second channel. The cutting guide may be positioned away from a vertebral body such that the distal face may be facing the vertebral body. The first and second channels may be oriented such that the first and second axes may extend distally towards each other and intersect at a distal point located in an interior of the vertebral body. The first cutting instrument may have a cross-section that is substantially the same as a cross-section of the first channel such that the first cutting instrument may be disposed in the first channel and guided along the first axis. The second cutting instrument may have a cross-section that is substantially the same as a cross-section of the second channel such that the second cutting instrument may be disposed in the second channel and guided along the second axis.

In accordance with the fourth aspect of the present invention, the first and second cutting instruments may have first and second stoppers, respectively to limit the distal movements of the first and second cutting instruments with respect to the cutting guide. The first and second cutting instruments may each have distal cutting edges which contact each other at the distal point. The cutting guide may further include a third slot extending from the proximal face to the distal face of the cutting guide having a third axis extending therethrough. The third axis may intersect with the first and second axes at the distal point. The surgical cutting assembly may further comprise a post that may be received in a third channel defined by the third slot. The post may have a threaded distal portion. A central portion of the post may include a distal locking element and a proximal locking element such that when the post is disposed in the third slot of the cutting guide, the cutting guide may be secured between the distal and proximal locking elements. A distal end of the third slot may include a counter bore to secure the distal locking element. The distal locking element may be a distal nut that may be received in the counter bore and the proximal locking element may include an externally threaded portion on the post that can threading engage with a proximal nut. The post may be cannulated to allow a guidewire to be inserted through the post. The surgical cutting guide may further include a fourth slot and a third cutting instrument. The fourth slot may extend from the proximal face to the distal face of the cutting guide. The fourth slot may be located between the first and second slot and defining a fourth channel to receive the third cutting instrument. A cross-section of the fourth slot may be substantially the same as a cross-section of the third cutting instrument to guide the third cutting instrument such that a distal end of the third cutting instrument may contact the first and second cutting instruments at the distal point.

In accordance with a fifth aspect of the present invention, method of performing a pedicle subtraction osteotomy procedure is provided. A method according to the fifth aspect may include the steps placing a vertical post in a vertebral body, inserting the vertical post in a first slot of a cutting guide and securing the cutting guide to the vertical post, inserting a first cutting instrument in a second slot of the cutting guide and distally advancing the first cutting instrument to a predetermined depth on a superior side of the vertical post, and inserting a second cutting instrument in a third slot of the cutting guide and distally advancing the second cutting equipment to the predetermined depth on an inferior side of the vertical post. The distal ends of the first and second cutting instruments may contact each other at the predetermined depth.

Further in accordance with the fifth aspect of the present invention, the step of placing a vertical post in a vertebral body may include positioning a threaded distal tip of the vertical post on the vertebral body and inserting the vertical post to the predetermined depth. The cutting guide may be secured to the vertical post by a proximal and a distal locking element. The first and second cutting instruments may include stoppers such that the stoppers prevents distal translation of the first and second cutting instruments with reference to the cutting guide at the predetermined depth.

Still further in accordance with the fifth aspect of the present invention, the method may include the step of inserting a third cutting instrument in a fourth slot of the cutting guide and distally advancing the third cutting instrument to the predetermined depth on a medial side of the vertical post to contact distal ends of the first and second cutting instruments. The fourth slot may be substantially transverse to the first and second slots. The method according to this aspect may further include the step of removing resected vertebral body by removing the vertical post with the attached cutting guide, first cutting instrument and the second cutting instrument.

In accordance with a sixth aspect of the present invention, method of performing a pedicle subtraction osteotomy procedure is provided. A method according to the fifth aspect may include the steps of placing a first cutting instrument in a vertebral body, distally advancing the first cutting instrument to a predetermined depth, placing a first slot of a cutting guide over the first cutting instrument, inserting a second cutting instrument in a second slot of the cutting guide and distally advancing the second cutting equipment to the predetermined depth on an inferior side of the cutting guide. The first slot may be located on a superior side of the cutting guide. The distal ends of the first and second cutting instruments may contact each other at the predetermined depth.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIG. 10 is a cross-sectional view along line B-B of the cutting guide assembly of FIG. 7;

FIGS. 12A-C are schematic views of a method of performing a cutting procedure with cutting guide assembly of FIG. 7 according to one embodiment of the present invention;

FIGS. 13A-13D are schematic front views of the cutting guide of FIG. 1 showing the sequential steps of performing a cutting procedure according to another embodiment of the present invention;

FIGS. 16A and 16B are schematic front views of the cutting guide of FIG. 15 showing the sequential steps of performing a cutting procedure according to another embodiment of the present invention;

FIG. 19 is a perspective view of a cutting guide according to another embodiment of the present invention;

FIG. 20 is a schematic front view of the cutting guide of FIG. 19 showing a cutting procedure according to another embodiment of the present invention;

DETAILED DESCRIPTION

Reference will now be made in detail to the preferred embodiments of the present invention illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import.

In describing preferred embodiments of the disclosure, reference will be made to directional nomenclature used in describing the human body. It is noted that this nomenclature is used only for convenience and that it is not intended to be limiting with respect to the scope of the invention. For example, as used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the head and the term "inferior" means more distant from the head.

Figure 1:
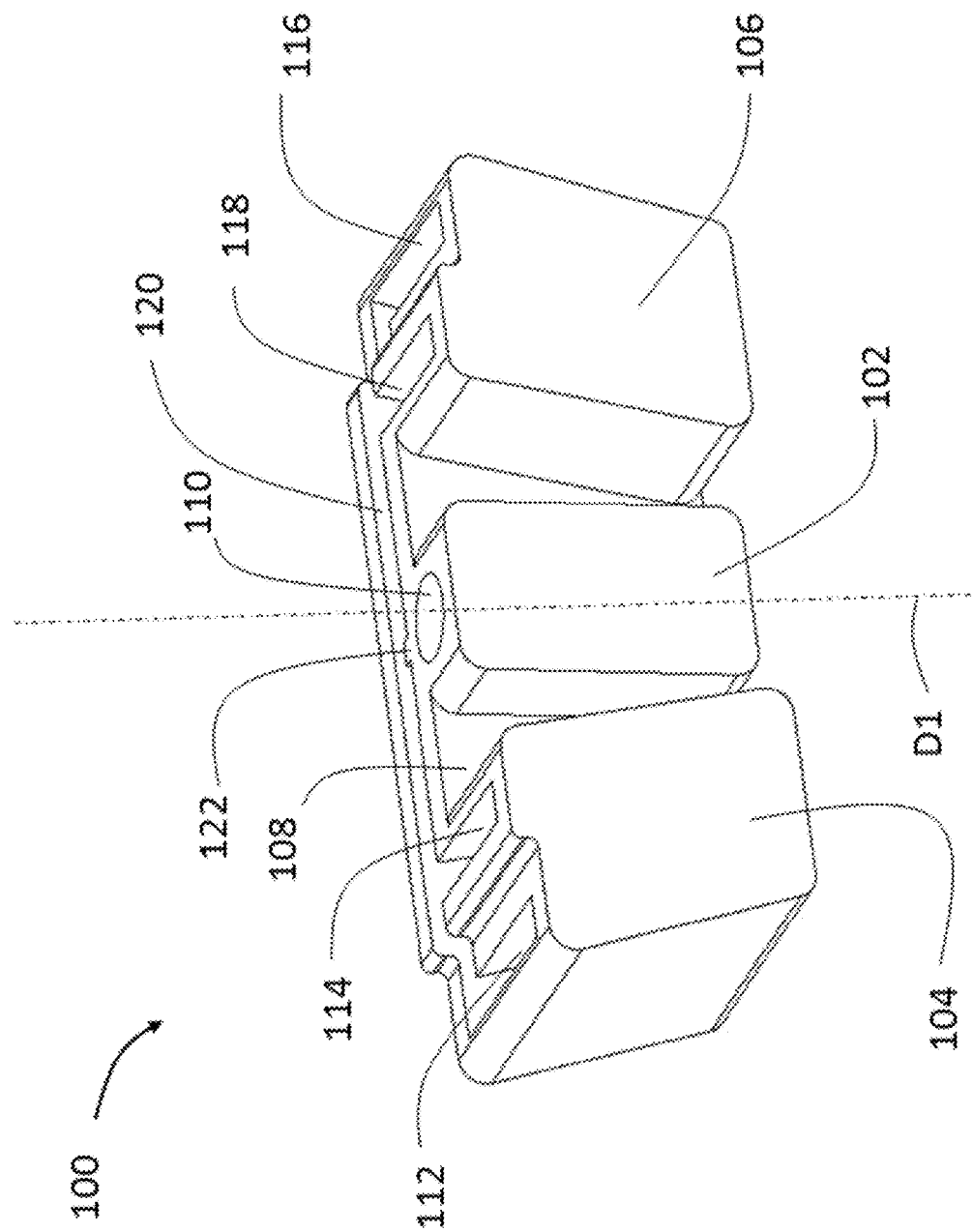
FIG. 1 is a perspective view of a cutting guide according to a first embodiment of the present invention.

FIG. 1 shows a perspective view of a cutting guide 100 according to one embodiment of the present invention. Cutting guide 100 includes a central rib 102, a superior rib 104 and an inferior rib 106 connected to a wall 108. Central rib 102 includes a central slot 110 defining a channel with an axis D1. A first superior slot 112 and a second superior slot 114 are located on a superior side of cutting guide 100. Similarly, a first inferior slot 116 and a second inferior slot 118 are located on an inferior side of cutting guide 100. A fourth longitudinal slot 120 is provided along a medial side of the cutting guide transverse to the inferior and superior slots. Longitudinal slot 120 includes a tongue 122 extending medial-laterally into slot 120 as best shown in FIG. 1. Each of these slots define channels which are oriented to receive and guide various surgical instruments and accessories, as more fully described below. Alternatively, the orientation of these slots may be adjustable such that they can be rotated or otherwise moved within their respective ribs to receive and guide various surgical instruments at different angles.

Figure 2:
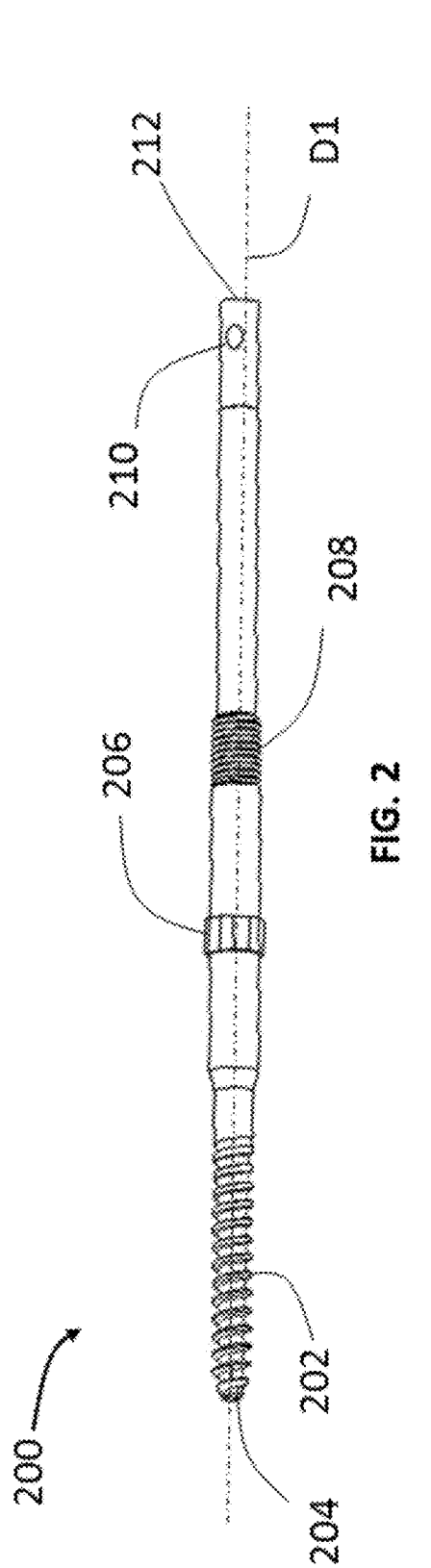
FIG. 2 is a front view of a post according to a first embodiment of the present invention.

FIG. 2 shows a side view of a post 200 according to an embodiment of the present invention. Post 200 has a generally circular cross-section and can be inserted into central slot 110 of cutting guide 100. A threaded distal end 202 of post 200 can be inserted into bone or other structures to anchor post 200. Post 200 is cannulated to allow a guidewire 500 to be inserted through the post. A quick release feature 212 located on a proximal end of post 200 allows for a handle (not shown) to be readily attached and detached from the post. A central portion of post 200 is shaped as a hexagonal nut 206 and can be received in a counter bore 124 (best shown in FIG. 10) of cutting guide 100 to prevent distal and rotational translation of post 200 with respect to cutting guide 100. While the hexagonal nut 206 shown in this embodiment is integral to post 200, other embodiments may have a hexagonal nut that can be threadingly engaged to post 200. An externally threaded portion 208 is located proximally to hexagonal nut 206 to allow the cutting guide 100 to be secured to post 200 once the cutting guide is placed on hexagonal nut 206.

Figure 3:
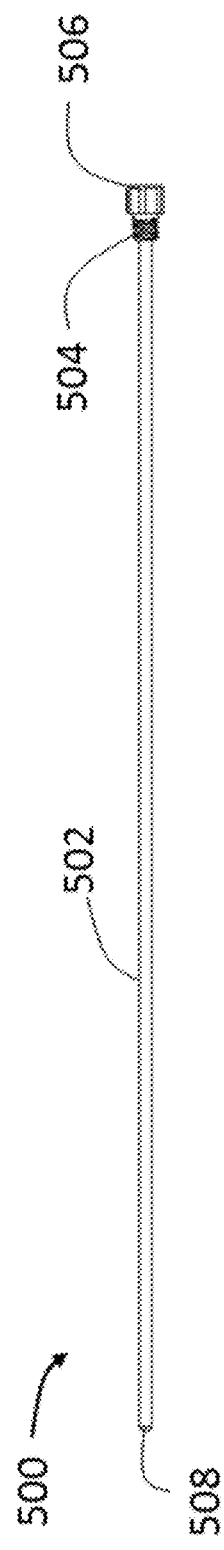
FIG. 3 is a front view of a guidewire to be used in conjunction with the post of FIG. 2.
Figure 4:
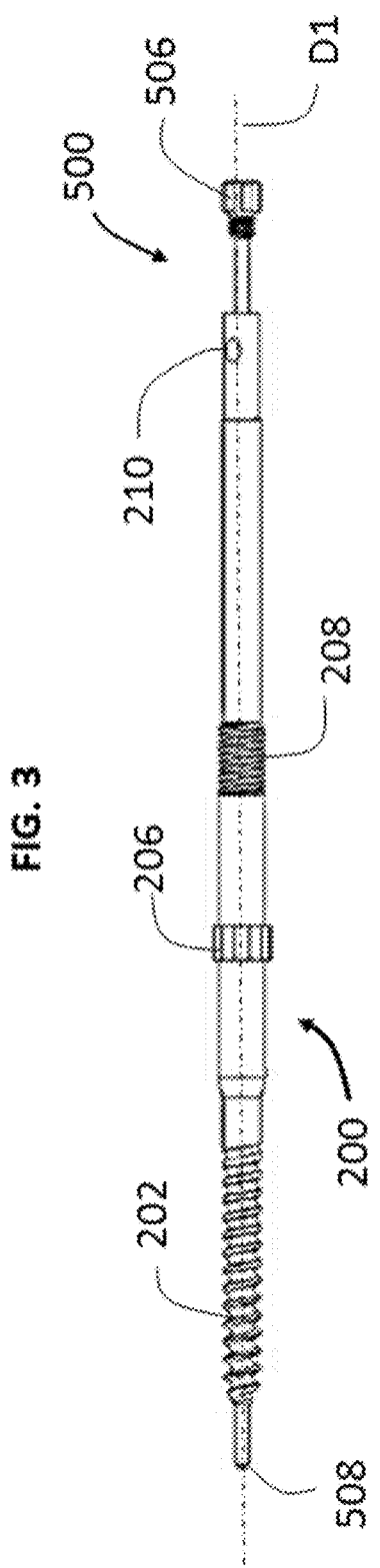
FIG. 4 is a front view of the post of FIG. 2 and the guidewire of FIG. 3.

FIG. 3 shows a side view of guidewire 500. Guidewire 500 has a long solid/cylindrical body 502 with a distal tip 508. Distal tip 508 may include radiopaque or radiolucent markers for x-ray imaging or other visualization techniques for precise placement of guidewire 500. In other embodiments, the entire guidewire may be radiopaque or have radiolucent markers located at different locations across the guidewire. Guidewire 500 also includes a threaded head portion 504 with a grippable head 506 to allow a user to secure guidewire 500 to post 200. As shown in FIG. 4, guidewire 500 can be inserted through post 200 such that distal tip 508 extends from a tip 204 of post 200. As more fully explained below, distal tip 508 marks the depth and defines the vertex of the resection cut during a PSO. Grippable head 506 can be used to threadingly engage guidewire 500 to post 200 to firmly secure the guidewire to the post. While a guidewire is shown in this embodiment, a probe, tap, drill, navigation tracker or other similar surgical tools may be placed in post 200.

Figure 5:
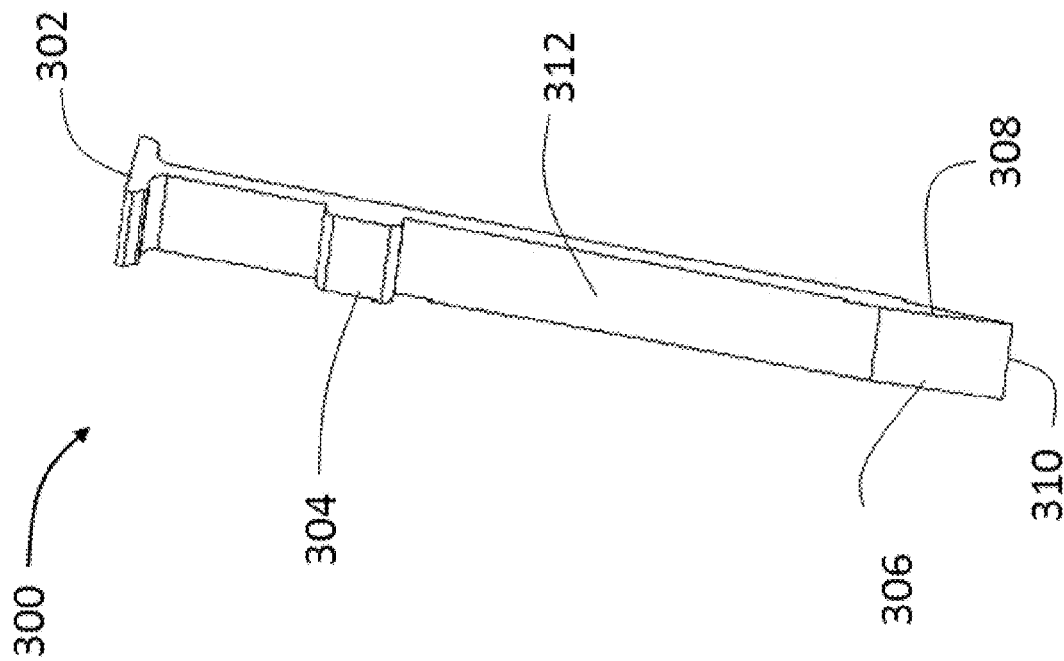
FIG. 5 is a perspective view of a transverse cutting instrument according to an embodiment of the present invention.

Referring now to FIG. 5, there is shown a perspective view of a transverse cutting instrument 300 according to one embodiment of the present invention. Transverse cutting instrument 300 as shown herein is an osteotome, but it can take the form of any other bone or tissue cutting surgical instrument. Transverse cutting instrument 300 has a generally flat body 312 with a cross-section that is substantially the same as the cross-section of inferior and superior slots 112, 114, 116, 118 of cutting guide 100 and can therefore be inserted into any one of these slots. A mallet or a slap-hammer can be used on a flat head surface 302 of transverse cutting instrument 300 to force the cutting instrument distally to perform the cutting procedure. A stopper 304 located on a proximal end of transverse cutting instrument 300 predetermines the distal translation of the cutting instrument with respect to cutting guide 100. While the placement of distal tip 508 of guidewire 500 defines the cutting depth, the location of the stopper may also be pre-operatively determined and set depending on the depth of the cut required to further ensure that the PSO achieves precise cutting depth. It is contemplated to have stopper 304 be a variable element, such that a surgeon can change the overall amount of distal translation of cutting instrument 300 for a given surgery. A tapered distal end 306 includes a cutting edge 310 as best shown in FIG. 5. The tapered shape of distal end 306 facilitates the cutting procedure by reducing bone resistance and increasing the cutting effect. Medial and lateral sides 308 of the transverse cutting guide may be blunt surfaces to minimize damage to surrounding tissue during the cutting operation.

Figure 6:
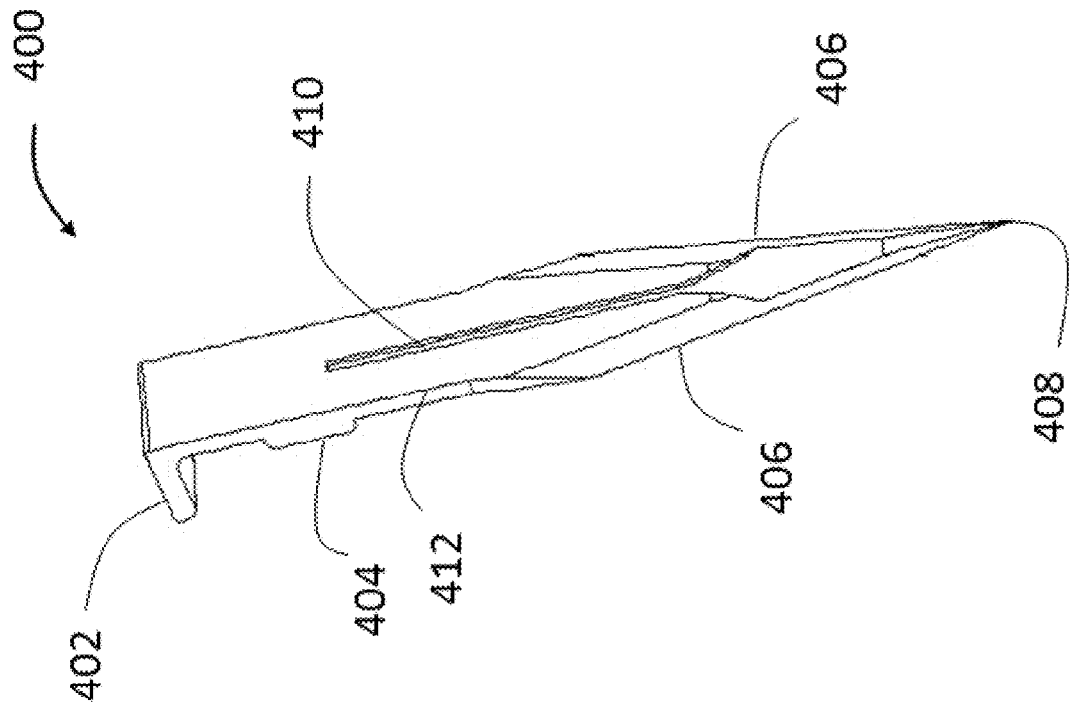
FIG. 6 is a perspective view of a medial cutting instrument according to an embodiment of the present invention.

FIG. 6 shows a perspective view of a medial cutting instrument 400 according to an embodiment of the present invention. Medial cutting instrument 400 has a generally flat body 412 with a cross-section that allows the medial cutting instrument to be placed in longitudinal slot 120 of cutting guide 100. A groove 410 of medial cutting instrument 400 is configured to engage with tongue 122 of cutting guide 100 when the medial cutting instrument is disposed in longitudinal slot 120. The tongue and groove engagement ensures that cutting guide 100 guides medial cutting instrument 400 to translate proximal-distally within longitudinal slot 120 and also limit superior-inferior translation and angulation of the medial cutting instrument. A mallet or a slap-hammer can be used on a flat head surface 402 of medial cutting instrument to force the cutting instrument distally to perform the cutting procedure. A stopper 404 located on a proximal end of the medial cutting instrument 400 predetermines the distal translation of the cutting instrument with respect to cutting guide 100. The location of the stop can be pre-operatively determined and set depending on the depth of the cut required. The pre-determined stop location in conjunction with distal tip 508 of guidewire can be used to precisely locate and ensure that cutting depth is achieved during a PSO. As with cutting instrument 300, stopper 404 can be variable. A tapered distal end 406 includes cutting edges 406 with a distal tip 408 as best shown in FIG. 6. Proximal-distal translation of cutting instruments disposed in any of the slots of cutting guide 100 may be achieved by impaction, sawing, splitting, ablation, abrasion milling, acoustic, pressure or any other means to perform the cutting operation.

Figure 7:
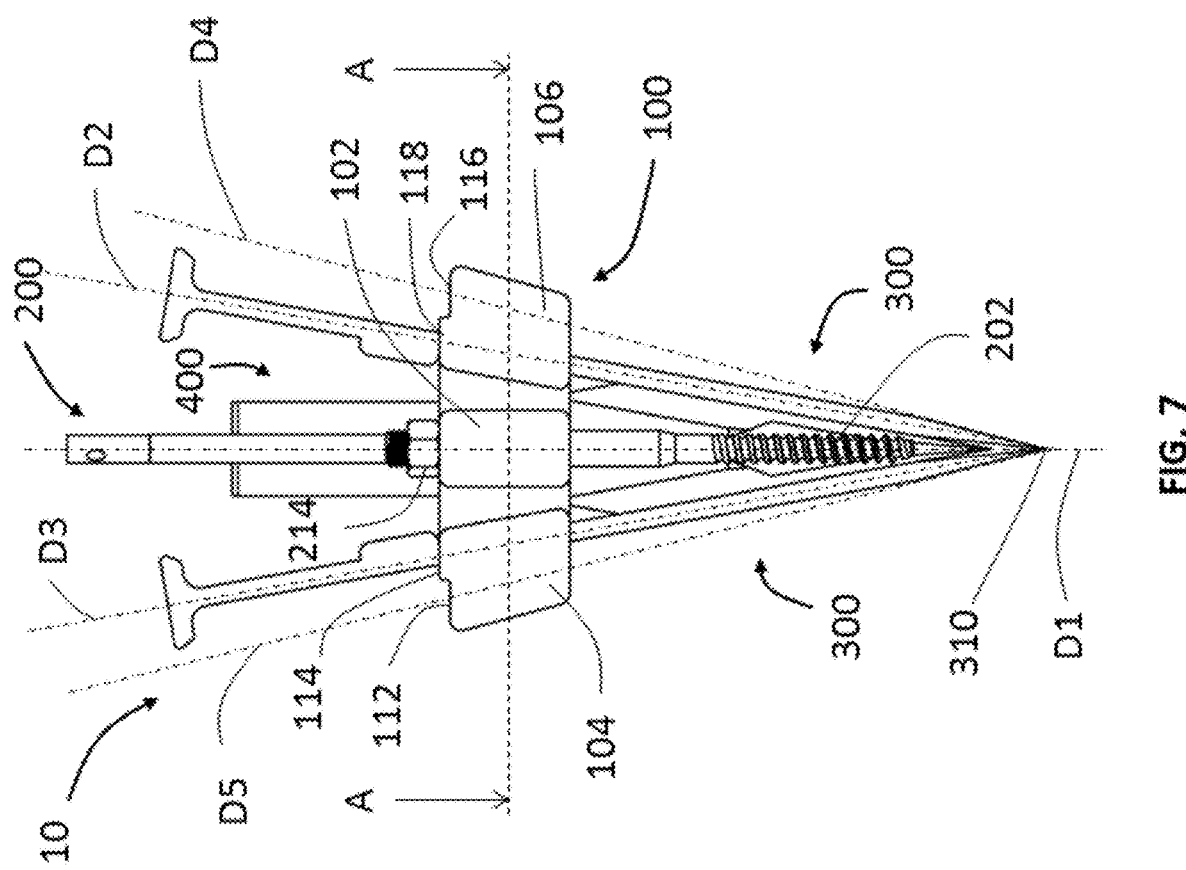
FIG. 7 is a front view of a cutting guide assembly with the transverse cutting instruments of FIG. 5 positioned in a first configuration according to an embodiment of the present invention.
Figure 8:
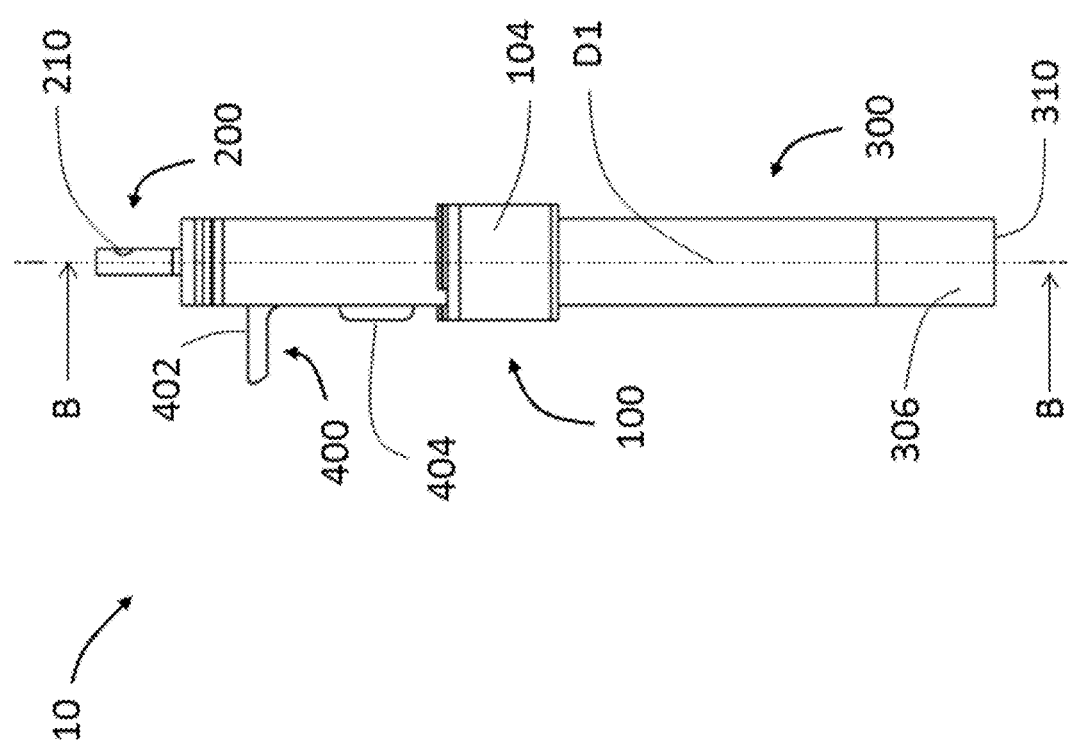
FIG. 8 is a side view of the cutting guide assembly of FIG. 7.

Referring now to FIGS. 7 and 8, there is shown front and side views of a cutting guide assembly 10 according to an embodiment of the present invention. Cutting guide assembly 10 may be used in a PSO and includes cutting guide 100, post 200, transverse cutting instruments 300 and medial cutting instrument 400. A first transverse cutting instrument 300 is inserted in second superior slot 114 and a second transverse cutting instrument 300 is inserted in second inferior slot 118 in cutting guide 100. Transverse cutting instruments 300 may be inserted in other superior and inferior slots of cutting guide 100 in other embodiments to vary the subtraction angles for the PSO. For example, inserting transverse cutting instruments 300 in first superior slot 112 and first inferior slot 116 will allow for a PSO procedure with a greater subtraction angle. Stoppers 304 have a larger cross-sectional area than flat surface 312 of transverse cutting instruments 300 and thereby distal translation of cutting instruments is restricted to a predetermined depth based on the stopper position and guidewire tip depth. As best shown in FIGS. 7 and 8, when transverse cutting instruments 300 are distally advanced, cutting edges 310 of both cutting instruments may contact each other. Stoppers 304 prevent any further distal translation of transverse cutting instruments 300 beyond this point. This allows a surgeon to insert and advance each transverse cutting instrument 300 individually to the precise depth required to complete the PSO.

Medial cutting instrument 400 is inserted into longitudinal slot 120 by ensuring that tongue 110 is engaged in groove 410. The tongue-groove engagement ensures precise proximal-distal translation of the medial cutting instrument 400. Stopper 404 on medial cutting instrument 400 is similar to stoppers 304 on transverse cutting instrument 300 and allows for an accurate distal penetration depth of the medial cutting instrument. In this embodiment, stopper 404 ensures that distal tip 408 of medial cutting instrument 400 contacts cutting edges 310 of both transverse cutting instruments 300 when advanced distally. Flat head surface 404 provides access for surgical impaction tools such as a slap hammer or mallet to advance medial cutting instrument 400.

Post 200 is disposed in central slot 110 of cutting guide 100 in cutting guide assembly 10. Hexagonal nut 206 of post 200 is seated in counterbore 124 of cutting guide 100 and prevents distal and radial translation of the cutting guide with respect to post 200. On the opposite proximal surface of the cutting guide 100, a nut 214 engages with threaded portion 208 of vertical post to secure cutting guide 100 to the post and prevent proximal translation.

Figure 9:
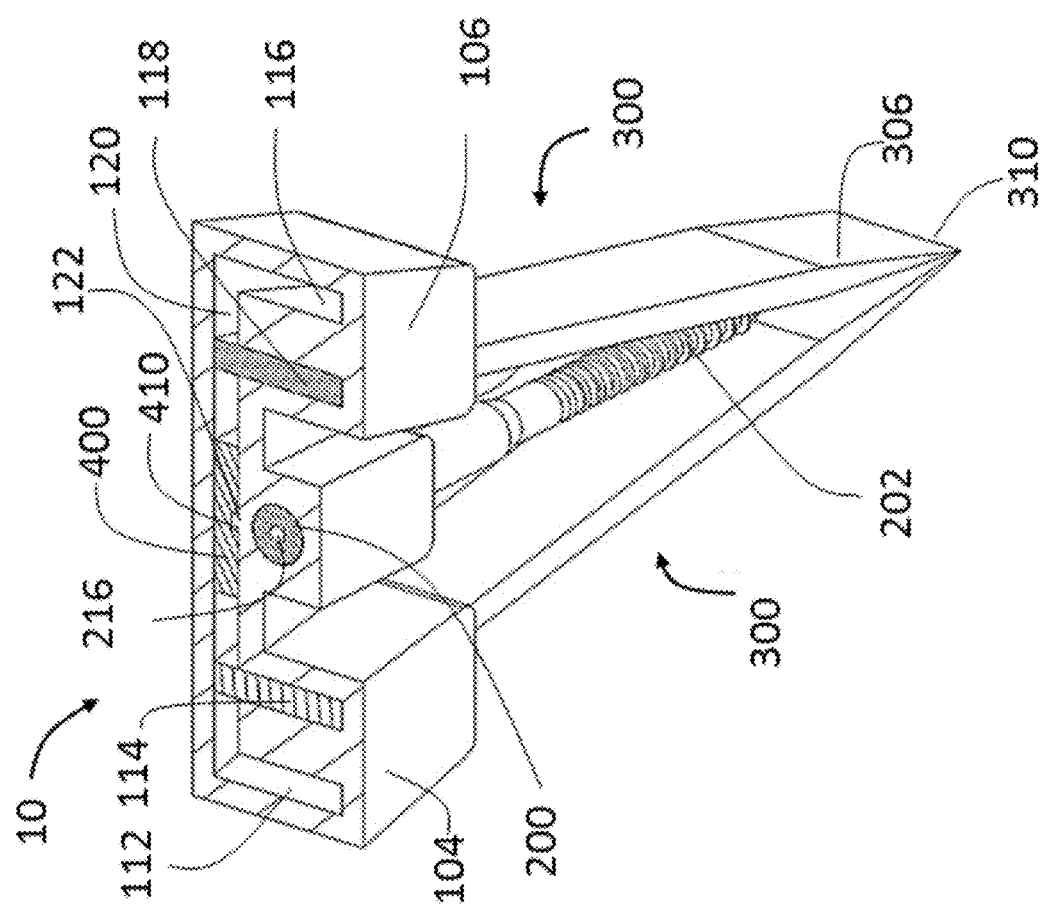
FIG. 9 is a cross-sectional view along line A-A of the cutting guide assembly of FIG. 7.

FIG. 9 shows a cross-sectional view of cutting guide assembly 10 along line A-A of FIG. 7. Cross-sectional areas of the flat surface 312 of transverse cutting instruments 300 are substantially similar to the cross-sectional areas of superior slot 114 and inferior slot 118. As shown herein, once the transverse cutting instruments 300 are placed in their respective slots, the slots are configured to encase and support the transverse cutting instruments with minimal clearance. This sliding fit between cutting guide 100 and transverse cutting instrument 300 ensures high precision in advancing the cutting instruments in a proximal-distal direction within their respective slots. The enlarged cross-sectional area of stopper 304 prevents distal translation beyond a predetermined depth. Similarly, the cross-sectional area of longitudinal slot 120 matches the cross-sectional area of medial cutting instrument 400 to facilitate a sliding fit between the medial cutting instrument and cutting guide 100. Furthermore, tongue 122 of longitudinal slot 120 is secured in groove 410 of medial cutting instrument 400 to ensure accurate proximal-distal translation of the cutting tool with respect to cutting guide 100. Also shown in FIG. 9 is a cross-section of the post 200 in central slot 110. Post 200 is slidably disposed within central slot 110 and allows for precise proximal-distal translation of post 200 along axis D1 with respect to cutting guide 100. A central channel 216 allows for guidewire 500 or any other instruments such as a probe to be disposed within post 200.

Referring now to FIG. 10, there is shown a front cross-sectional view of cutting guide assembly 10 along line B-B of FIG. 8. Each of the superior and inferior slots 112, 114, 116, 118 define internal channels oriented along an axis. First superior slot 112 is oriented along axis D5, second superior slot 114 is oriented along axis D3, first inferior slot is oriented along axis D4 and second inferior slot is oriented along axis D5. Axes D2, D3, D4 and D5 extend distally and toward a central axis D1 defined by central slot 110 to intersect at distal point D8. PSO subtraction angle can be varied by inserting transverse cutting instruments in various slots. For example, a subtraction angle A1 defined by axis D5 and axis D4 when the transverse cutting instruments are placed in first inferior slot 116 and first superior slot 112 is larger than a subtraction angle A2 defined by axis D2 and axis D3 when the transverse cutting instruments are placed in second inferior slot 118 and second superior slot. As shown in FIG. 10, transverse cutting instrument 300 is placed in second inferior slot 118 and therefore defines a smaller subtraction angle A2 on the superior and inferior sides. Cutting guide subtraction angle A1 according to this embodiment may generally range from 30 to 45 degrees, and subtraction angle A2 may generally range from 20 to 30 degrees. As with other embodiments according to the present invention, these dimensions may vary widely depending upon the specific application.

As best shown in FIG. 10, counterbore 124 of cutting guide 100 receives hexagonal nut 206 and prevents distal and rotational translation of the cutting guide with reference to post 200. Nut 214 on an opposite side of counterbore 124 is threadingly engaged with threaded portion 208 of post 200 to prevent proximal displacement of the cutting guide with reference to post 200. Hence, the two locking mechanisms on either side of the cutting guide, i.e., hexagonal nut-counterbore 206-124 and nut-threaded portion 214-208, secure cutting guide 100 to post 200. Other locking mechanisms such as a ball and detent may also be used to secure cutting guide 100 to post 200. Also shown in FIG. 10 is an internally threaded portion 126 of post 200 to threadingly engage with external threaded head 504 of guidewire 500.

Figure 11B:
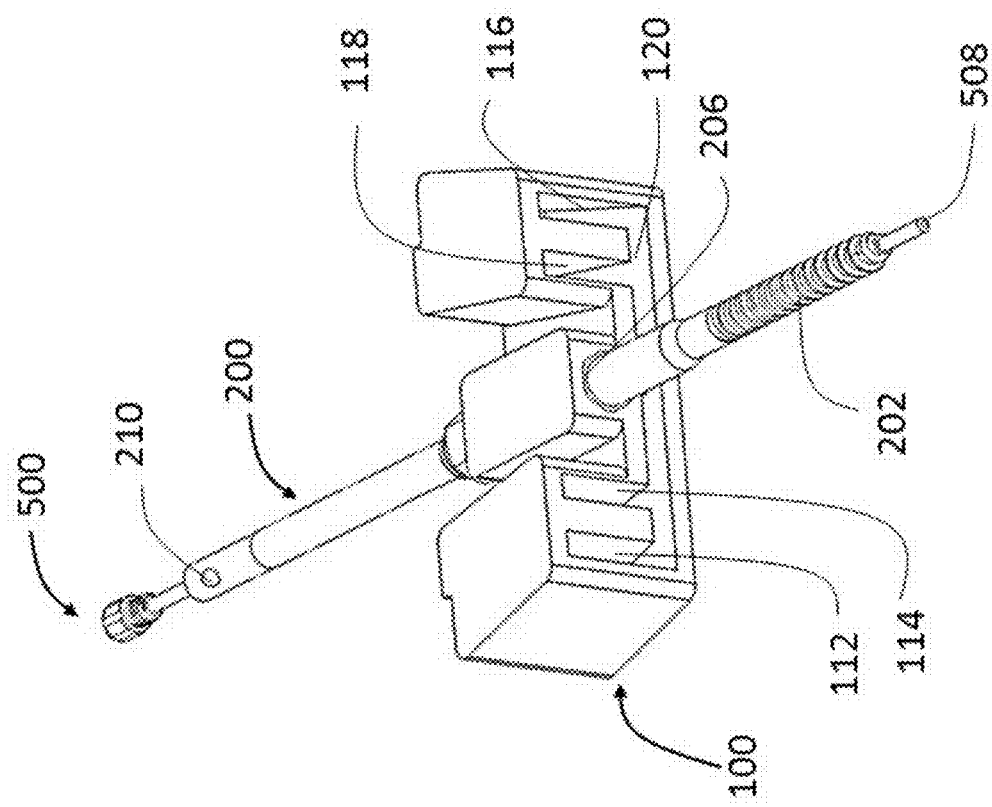
FIG. 11B is a perspective view of the cutting guide, post and guidewire of FIG. 11A.
Figure 11A:
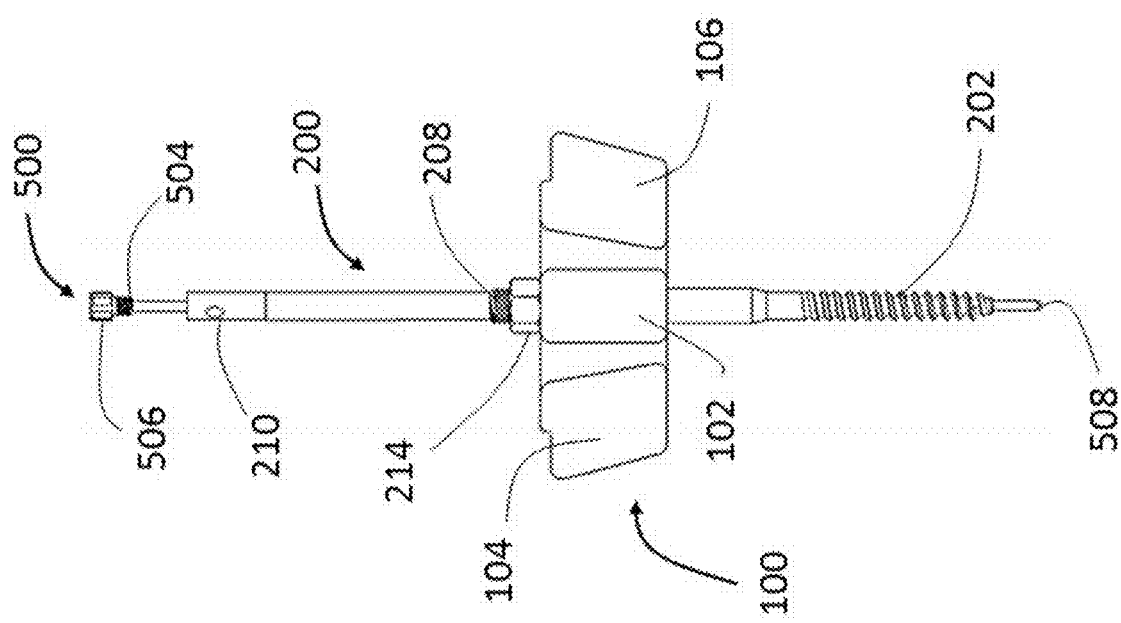
FIG. 11A is a front view of the cutting guide of FIG. 1 in conjunction with the post and guidewire of FIG. 4.

FIGS. 11A and 11B show front and perspective views of cutting guide 100 secured to post 200 and guidewire 500. Guidewire 500 may be placed in internal channel 216 of post 200 such that distal end 508 extends distally away from tip 204 of post 200. The guidewire and post assembly can be advanced into the vertebral body to the required cutting depth defined by distal tip 508 of guidewire 500. Alternatively, a surgeon may first place distal end 508 at a target surgical site and then slide post 200 around the anchored guidewire 500. As more fully explained above, grippable head 506 can be used to secure externally threaded portion 504 to internal threading 126 of post 200. A quick release mechanism such as a snap-fit, ratchet or other similar mechanisms may be used to quickly disconnect the threading engagement of post 200 from guidewire 500 to remove either of them with respect to the other. As best seen in FIG. 11B, a perspective view of the distal face of cutting guide 100 shows the inferior slots 112, 114, superior slots 116, 118, longitudinal slot 120 and central slot 110. Hexagonal nut 206 seated in counterbore 124 prevents distal and rotational translation of cutting guide 100 with respect to post 200.

FIGS. 12A-C show a method for performing a PSO using cutting guide assembly 10 according to one embodiment of the present invention. Guidewire 500 is inserted into internal channel 216 of post such that distal end 508 extends from distal tip 204. Distal end 508 is then and positioned at the target surgical site by distally advancing post 200 to penetrate vertebral body 22 of vertebra 20. Optical markers or other image assistance markers may be provided on distal end 508 to allow a surgeon to precisely positon post 200. Alternatively, guidewire 500 can first be advanced into vertebral body 22 to the target site and then post 200 can be slid over the guidewire. After post 200 has been threadingly secured to vertebral body 22 such that the distal tip 508 is located precisely at the required cutting depth, guidewire 500 is removed by unscrewing the grippable head 500 or by using a quick release feature 210 if provided. Cutting guide 100 is then slid over anchored post 200 until counterbore 124 is seated over hexagonal nut 206 to secure cutting guide 100 to post 200 and prevent distal and rotational translation of the cutting guide with the post. Nut 214 is placed over the post and secured to external threaded portion 208 to firmly press down on cutting guide 100 and prevent proximal translation of cutting guide 100 with respect to post 200. Hence, cutting guide 100 is now securely attached to anchored post 200 with no distal, proximal or rotational translation between the cutting guide and the post as best shown in FIG. 12A.

Transverse cutting instruments 300 are selected based on the cutting guide being used to ensure that the cutting instruments fit into the cutting guide slots. Stopper 304 placements on transverse cutting instruments 300 may also be considered in selecting the appropriate cutting instrument. As more fully explained above, stopper 304 placement on transverse cutting instrument 300 may aid in determining the cutting depth. Transverse cutting instruments 300 with fixed stoppers allowing for various predetermined cutting depth may be provided in a kit, or a transverse cutting instrument with an adjustable stopper may be provided to further assist a surgeon in achieving the cutting depth and trajectory. A first transvers cutting instrument 300 is placed in any one of the inferior or superior slots depending on the subtraction angle required for the PSO. For example, placing the transverse cutting instrument 300 closer to central slot 110 will result in a smaller subtraction angle and conversely placing the cutting instrument away from central slot 110 will allow for greater subtraction angles. A mallet, slap hammer or other surgical impaction tools can be used to drive first transverse cutting instrument 300 to the target depth. Similarly, a second transverse cutting instrument can be placed in one of the opposite slots and distally driven into vertebral body 22 until stopper 304 of second transverse cutting instrument prevent further distal translation. At this point, cutting surface 310 of the second transverse cutting instrument contacts cutting surface 310 of the first transverse cutting instrument and thereby completes a V-shaped cut. Medial distal cutting instrument 400 is inserted in longitudinal slot 120 and driven distally until stopper 404 prevents further distal translation. Distal tip 408 at this point will contact cutting surfaces 310 of the first and second transverse cutting instruments and complete the cutting procedure. Threaded distal end 202 of post 200 will now be anchored to the resected bone and as such post 20 can now be used to remove resected bone 29 along with the cutting guide assembly 10 as shown in FIG. 12B. FIG. 12C shows the completed PSO resection wherein vertebral body 22 has a wedge-shaped hollow cut 28 defined by subtraction angle A1 and cutting depth D10.

Figure 13D:
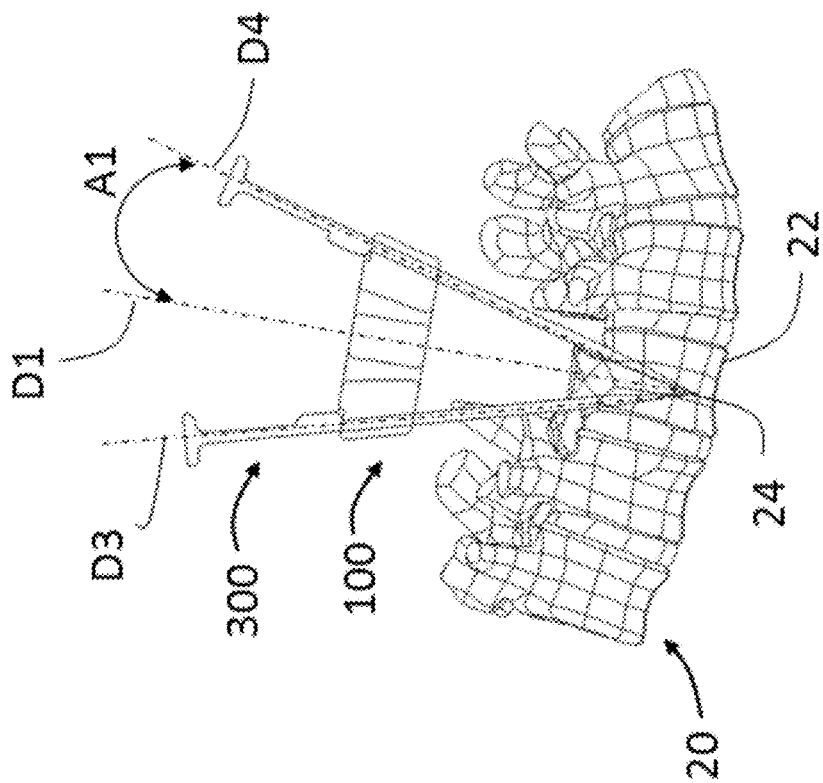

Referring now to FIGS. 13A-13D, there are shown schematic front views of a method for performing a PSO using cutting guide 100 and transverse cutting instruments according to another embodiment of the present invention. As shown in FIG. 13A, transverse cutting guide 300 is first placed on vertebral body 22 and inserted by using a surgical impaction tool such as a slap hammer or mallet to drive distal cutting surface to the required cutting depth 24. The angle of penetration is manually controlled without the aid of cutting guide reference. X-ray or other imaging systems may be used to aid a surgeon in placing transverse cutting instrument 300. Transverse cutting instrument 300 does not have an integral stopper as best shown in FIG. 13A. After placing the first transverse cutting instrument 300 at the required depth, cutting guide 100 is then placed over transverse cutting instrument 300 through first superior slot 112 as shown in FIG. 13B. Detachable flat surface 302 allow the cutting guide to be placed over the transverse cutting guide. A stopper 304 can be added to transverse cutting instrument 300 to prevent distal translation of the transverse cutting instrument with reference to the cutting guide.

Figure 13C:
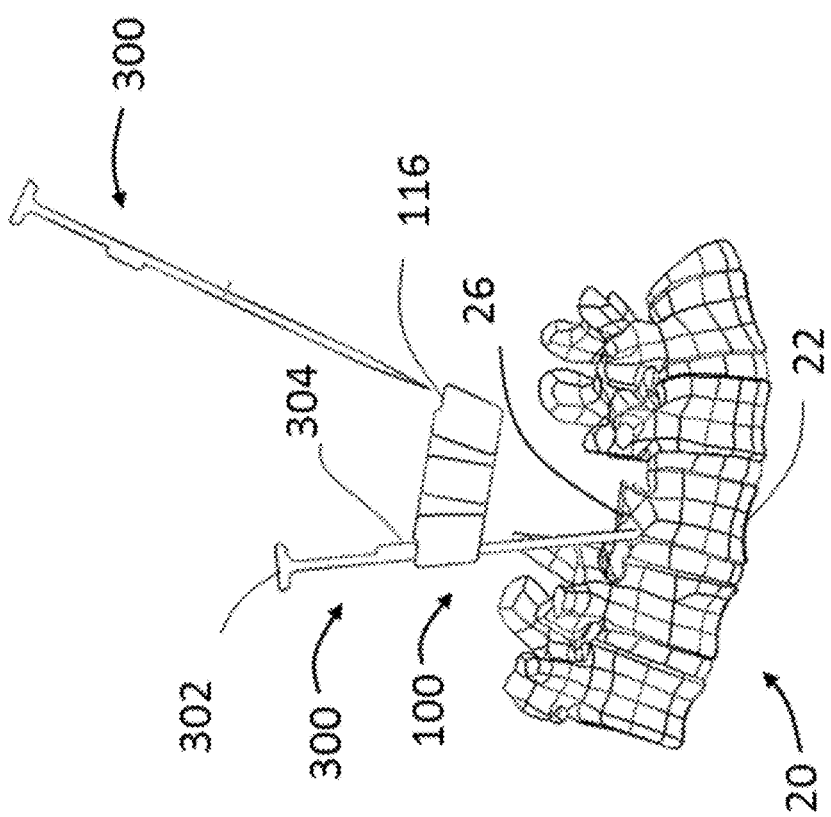

A second transverse cutting instrument is then inserted in first inferior slot 116 as shown in FIG. 13C. A mallet or slap hammer can be used to drive second transverse cutting instrument 300 distally until cutting surface 310 of the second transverse instrument contacts cutting surface 310 of the first transverse cutting instrument to complete the V-shaped PSO cutting procedure. As best shown in FIG. 13D, first and second transverse cutting instruments form angle A1 with respect to central axis D1. If a smaller subtraction angle, i.e., A2 is required, a surgeon may dock cutting guide 100 over the first transverse cutting guide using the second superior slot 114 and insert the second transverse cutting guide in second inferior slot 118 of cutting guide. Once the resection is complete, a surgeon may remove the resected bone by simply removing cutting guide and transverse cutting instrument assembly.

Figures 14A, 14B:
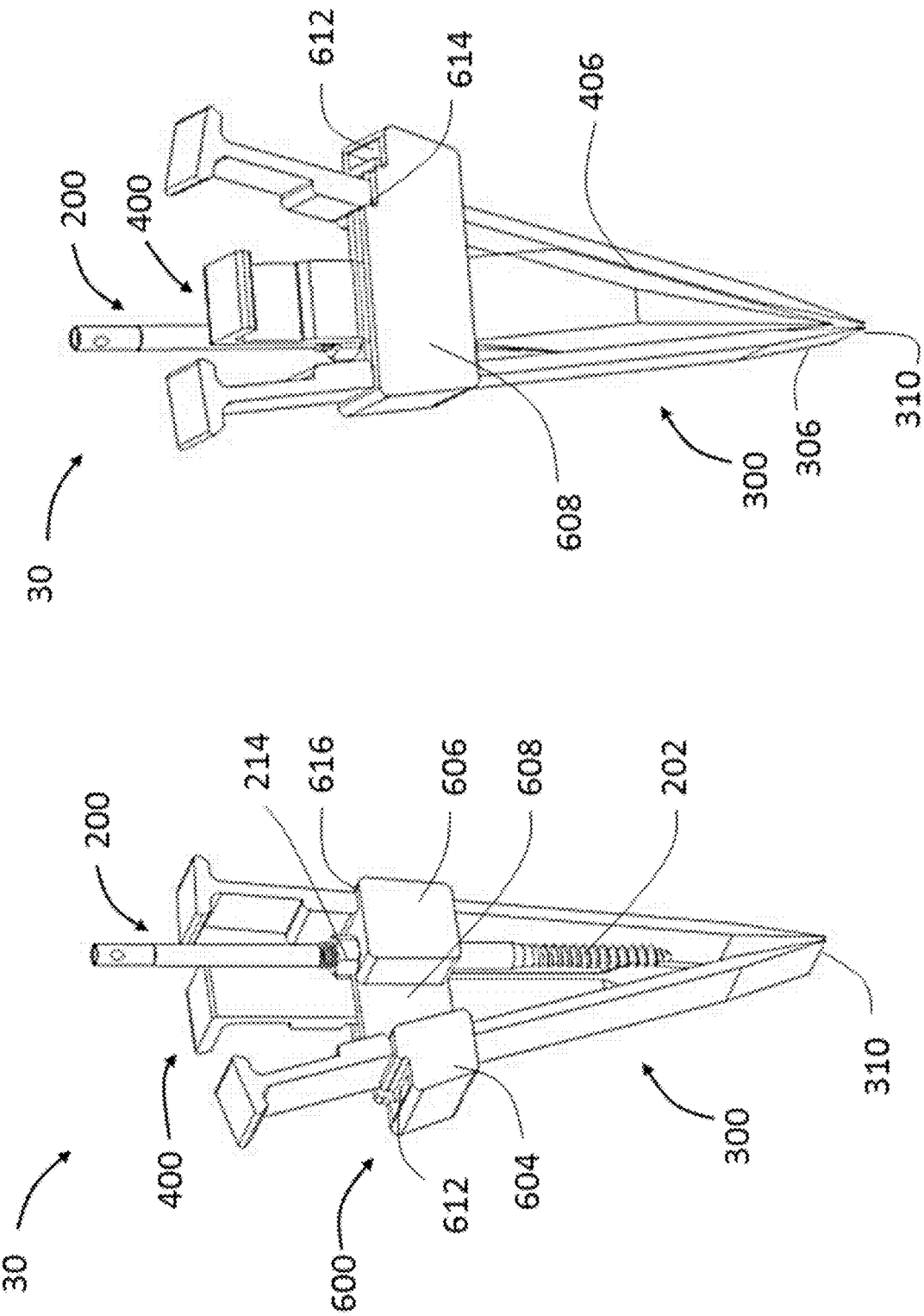
FIG. 14A is a front view of a cutting guide assembly with a cutting guide according to another embodiment of the present invention.
FIG. 14B is a back view of the cutting guide assembly of FIG. 14A.

FIGS. 14A and 14B show front and back views of a cutting guide assembly 30 according to another embodiment of the present invention. Cutting guide assembly 30 includes a cutting guide 600 with two transverse cutting instruments 300, medial cutting instrument 400, and post 200. Cutting guide 600 is similar to cutting guide 100, and therefore like elements are referred to with similar numerals within the 600-series of numbers. For instance, cutting guide 600 includes superior rib 604 with first superior slot 612 and second superior slot 614. However, cutting guide 600 does not have a central rib. Instead, central slot 610 is disposed within inferior rib 606 as best shown in FIG. 14A. Furthermore, there is only one inferior slot 616 in this embodiment. Cutting assembly 30 may be used in a PSO as more fully described above. Post 200 with guidewire 500 can be inserted into central slot 610 and used in performing the PSO. The single inferior slot located adjacent to the central slot 610 in the inferior rib of this embodiment offers a more rigid cutting guide assembly construct.

Figure 15:
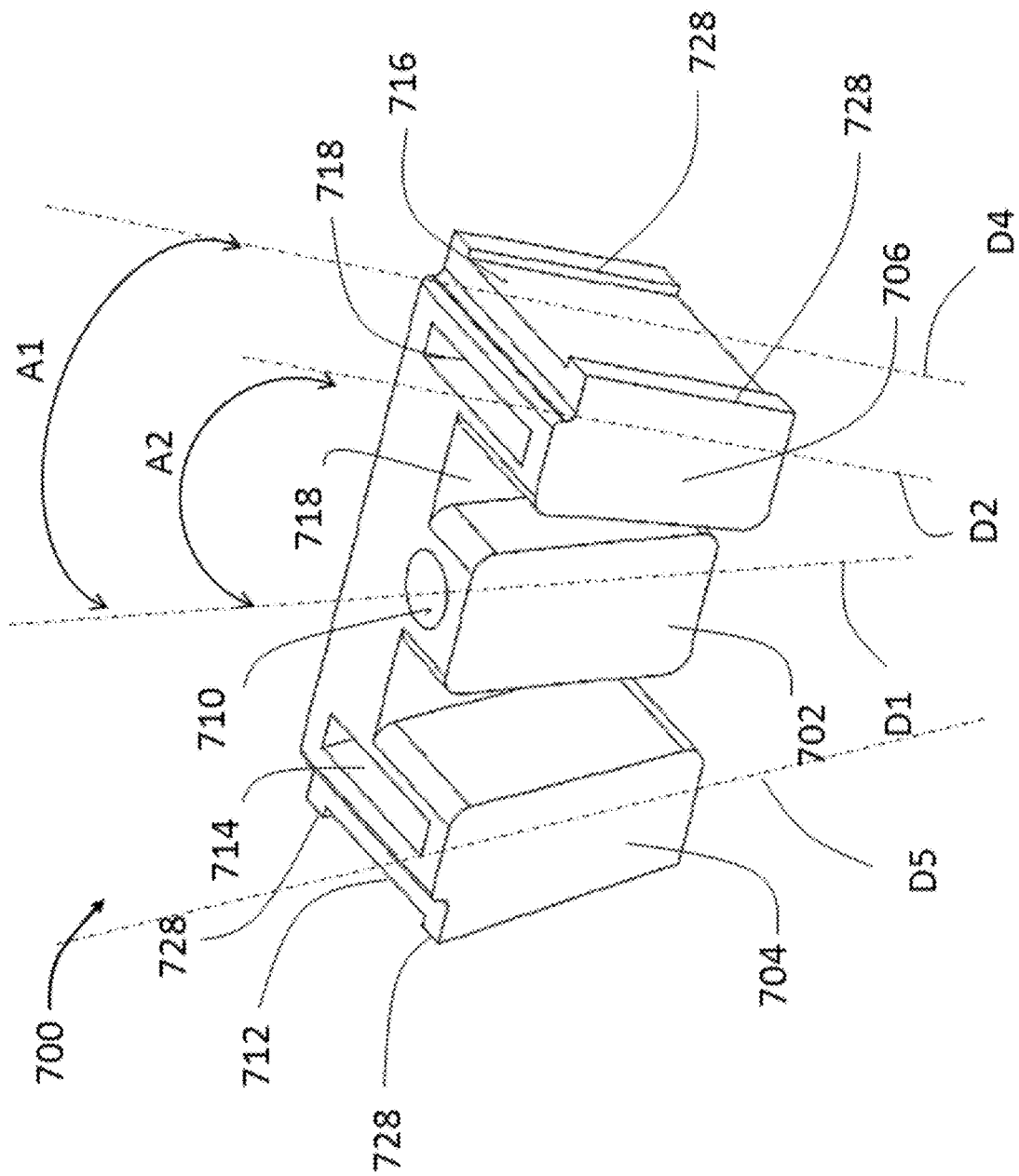
FIG. 15 is a perspective view of a cutting guide according to another embodiment of the present invention.

Referring now to FIG. 15, there is shown a cutting guide 700 according to another embodiment. Cutting guide 700 is similar to cutting guide 100, and therefore like elements are referred to with similar numerals within the 700-series of numbers. For instance, cutting guide 700 includes superior rib 704 with second superior slot 714 and inferior rib 706 with second inferior slot 718. However, cutting guide 700 does not have first superior and inferior slots. Instead, cutting guide 700 has a superior wall 712 and an inferior wall 716 as shown in FIG. 15. Superior wall 712 and inferior wall 716 surfaces are parallel to the respective superior and inferior slots. For instance, inferior wall 716 defines a plane with an axis D4. Axis D4 is parallel to axis D2 defined by inferior slot 718. Therefore, axis D5 defined by superior wall 712 and axis D4 converge at a common distal point D8 (not shown). Common distal point D8 will correspond to distal tip 508 of guidewire 500. Superior wall 712 and inferior wall 716 include peripheral ridges 728 that run from the proximal to the distal face of the cutting guide 700. The gap between the ridges is configured to receive and guide transverse cutting instruments. While peripheral ridges 728 extending between the proximal and distal face of cutting guide 700 are shown in this embodiment, other embodiments may only have peripheral partially extending along the inferior and superior walls.

FIGS. 16A and 16B show a method for performing a PSO using cutting guide 700 according to another embodiment of the present invention. Guidewire 500 is inserted into internal channel 216 of post such that distal end 508 extends from distal tip 204. Distal end 508 is then positioned at the target surgical site by distally advancing post 200 to penetrate vertebral body 22 of vertebra 20. Optical markers or other image assistance markers may be provided on distal end 508 to allow a surgeon to precisely positon post 200. After post 200 has been threadingly secured to vertebral body 22 such that the distal tip 204 is located precisely at the required cutting depth, guidewire 500 is removed by unscrewing the grippable head 500 or using a quick release feature 210 if provided. Cutting guide 700 is then placed over anchored post 200 until counterbore 724 is seated over hexagonal nut 206 to secure cutting guide 100 to post 200 and prevent distal and rotational translation of the cutting guide with the post. Nut 214 is placed over the post and secured to external threaded portion 208 to firmly press down on cutting guide 700 and prevent proximal translation of cutting guide 700 with respect to post 200. Hence, cutting guide 700 is now securely attached to anchored post 200 with no distal, proximal or rotational translation between the cutting guide and the post.

Transverse cutting instruments 300 are selected based on the required cutting depth. (Not preferred) As more fully explained above, location of stopper 304 on transverse cutting instrument 300 determine the cutting depth. A first transvers cutting instrument 300 is placed on superior wall 712 of cutting guide 700. Transverse cutting instrument 300 is configured to fit within peripheral ridges 728 such that there is no clearance between peripheral ridges and the transverse cutting instrument when the cutting instrument is placed on superior wall 712. Hence, transverse cutting instrument 300 can slide across superior wall 712 and distally advanced along axis D5 while being confined within peripheral ridges 728. A mallet, slap hammer or other surgical impaction tools can be used to drive first transverse cutting instrument 300 to the target depth. Similarly, a second transverse cutting instrument can be placed on inferior wall 716 until stopper 304 of second transverse cutting instrument prevent further distal translation. At this point, cutting surface 310 of the second transverse cutting instrument contacts cutting surface 310 of the first transverse cutting instrument and thereby complete a V-shaped cut as shown in FIG. 16B. Threaded distal end 202 of post 200 will now be anchored to the resected bone and as such post 200 can now be used to remove the resected bone along with the cutting guide 700.

Figure 17:
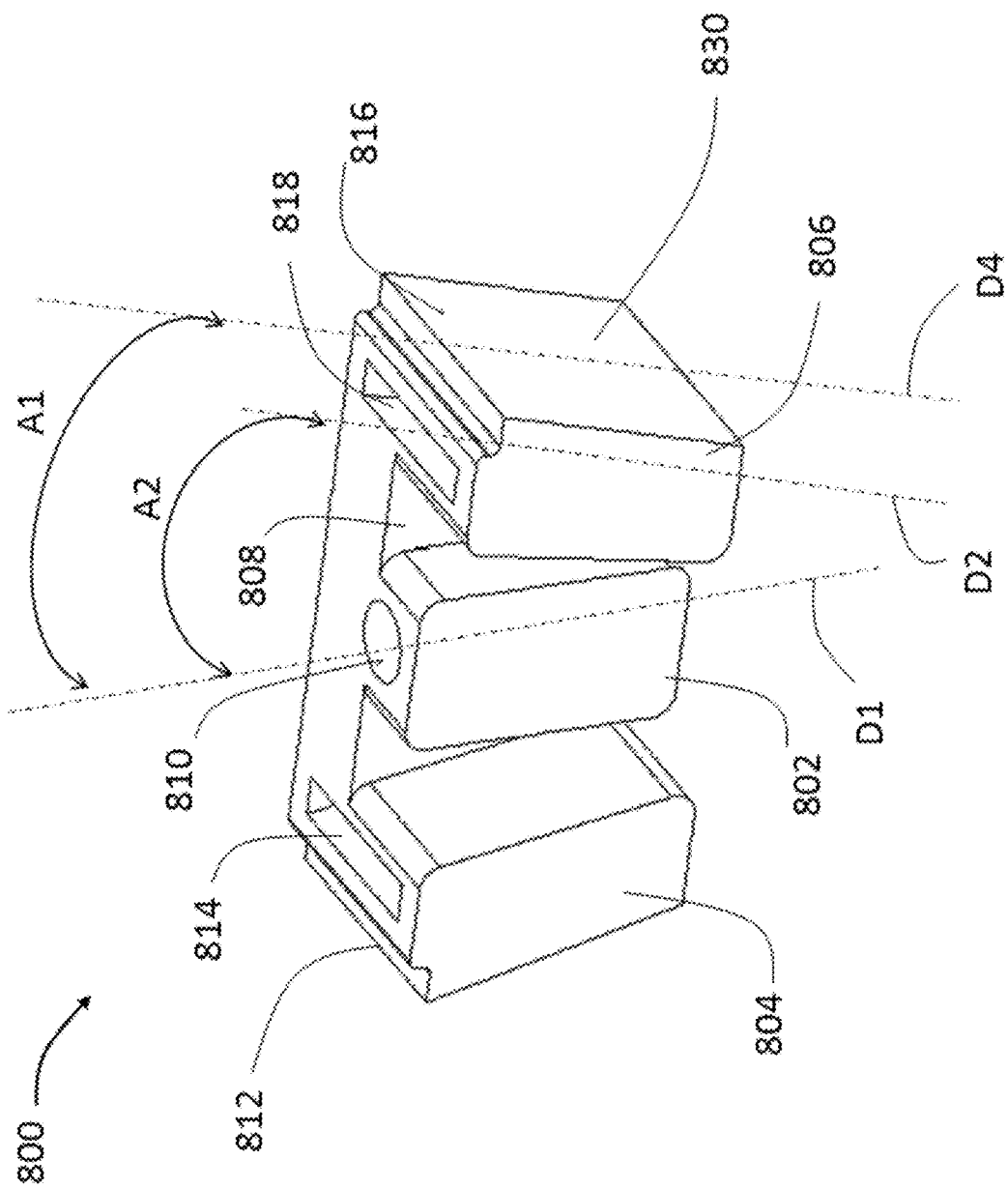
FIG. 17 is a perspective view of a cutting guide according to another embodiment of the present invention.

Referring now to FIG. 17, there is shown a cutting guide 800 according to another embodiment of the present invention. Cutting guide 800 is similar to cutting guide 700, and therefore like elements are referred to with similar numerals within the 800-series of numbers. For instance, cutting guide 800 includes superior rib 804 with superior wall 812 and inferior rib 806 with inferior wall 816. However, superior wall 812 and inferior wall 816 do not have peripheral ridges in this embodiment. Consequently, transverse cutting instrument do not require a specific width corresponding to the gap between the peripheral ridges to be used with cutting guide 800. Instead, transverse cutting guides with width not equal to the inferior or superior wall may be readily used in conjunction with cutting guide 800.

Figure 18B:
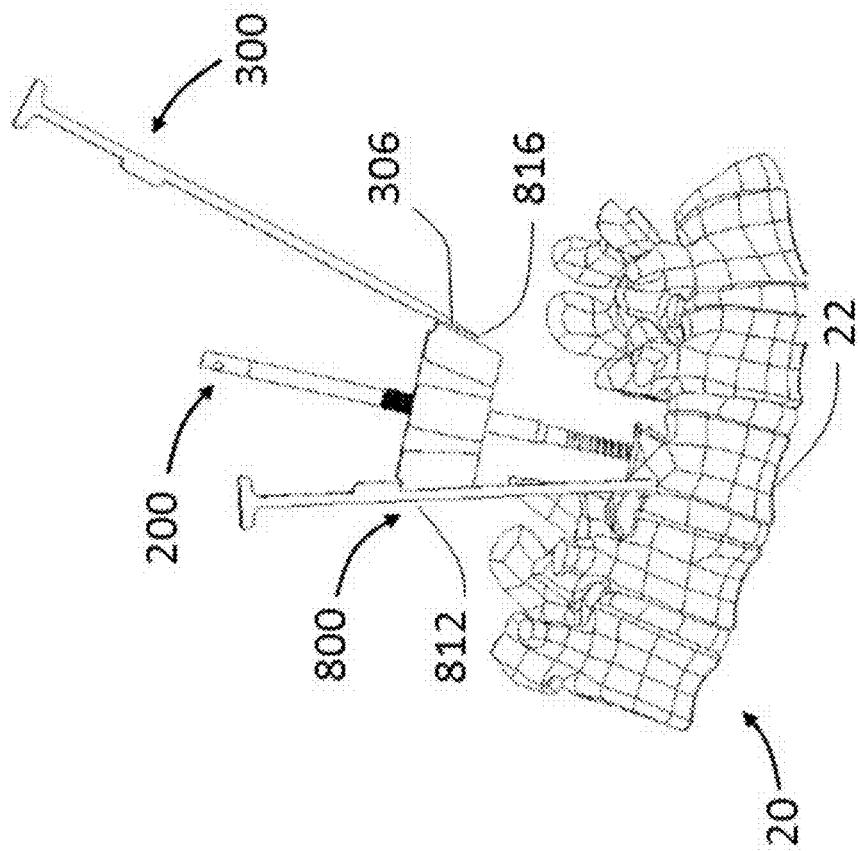
FIGS. 18A-18B are schematic front views of the cutting guide of FIG. 17 showing the sequential steps of performing a cutting procedure according to another embodiment of the present invention.
Figure 18A:
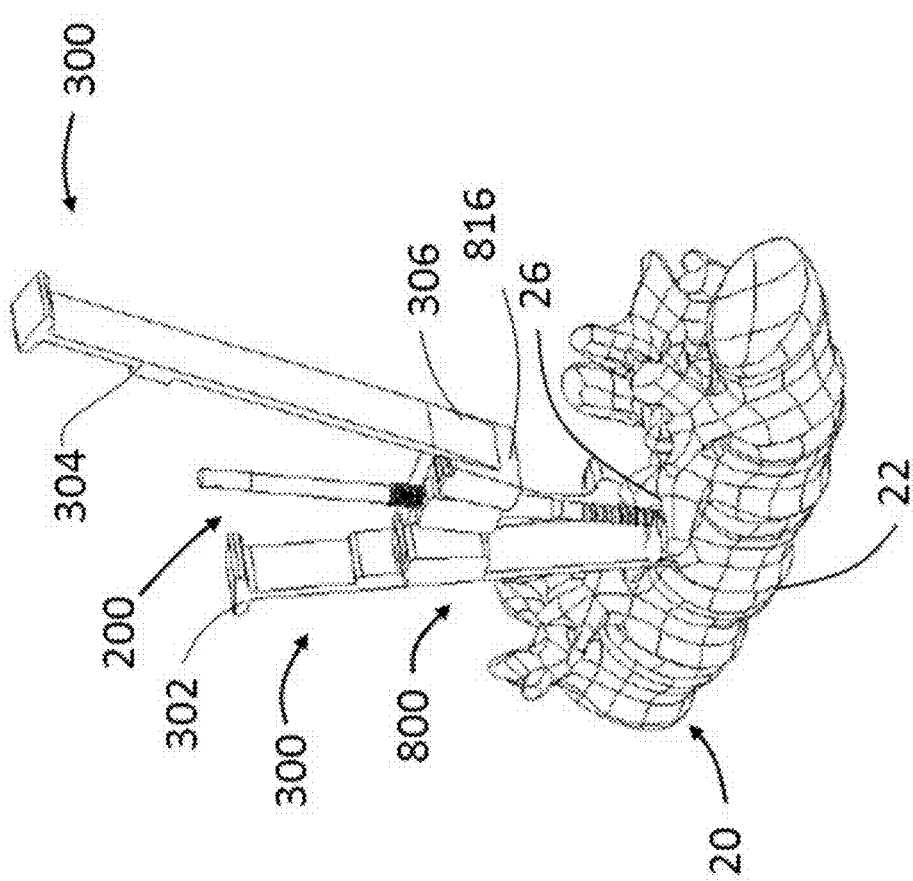

FIGS. 18A and 18B show a method for performing a PSO using cutting guide 800 according to another embodiment of the present invention. PSO using cutting guide 800 is similar to the procedure described with reference to cutting guide 700. However, transverse cutting instruments can be placed on superior and inferior walls and distally advanced. This allows a surgeon greater flexibility in placing and advancing the transverse cutting instruments. Furthermore, cutting guide 800 does not require cutting tools that are specifically sized to fit with the cutting guide. It is to be understood that cutting guide 800 could be designed to include a magnet or the like to aid in keeping cutting tools in concert with the guide.

FIG. 19 shows a cutting guide 900 according to another embodiment of the present invention. Cutting guide 900 is similar to cutting guide 800, and therefore like elements are referred to with similar numerals within the 900-series of numbers. For instance, cutting guide 900 includes superior rib 904 with superior wall 912 and inferior rib 906 with inferior wall 916. Cutting guide 900 includes a superior reference marker 914 parallel to superior wall 912 and an inferior reference maker 918 parallel to inferior wall 916. Reference markers 914 and 918 allow a surgeon to choose a desired subtraction angle. For example, transverse cutting instruments placed on the superior and inferior wall may defined a subtraction angle of 40 degrees, whereas cutting instruments placed along reference markers 914, 918 may define a subtraction angle of 25 degrees.

FIG. 20 show a method for performing a PSO using cutting guide 900 according to another embodiment of the present invention. PSO using cutting guide 900 is similar to the procedure described with reference to cutting guide 800. However, transverse cutting instruments can be placed on superior and inferior walls or along reference makers 914 and 918 and distally advanced. This allows a surgeon greater flexibility in placing and advancing the transverse cutting instruments and does not require cutting tools that are specifically sized to fit with the cutting guide.

Figure 21:
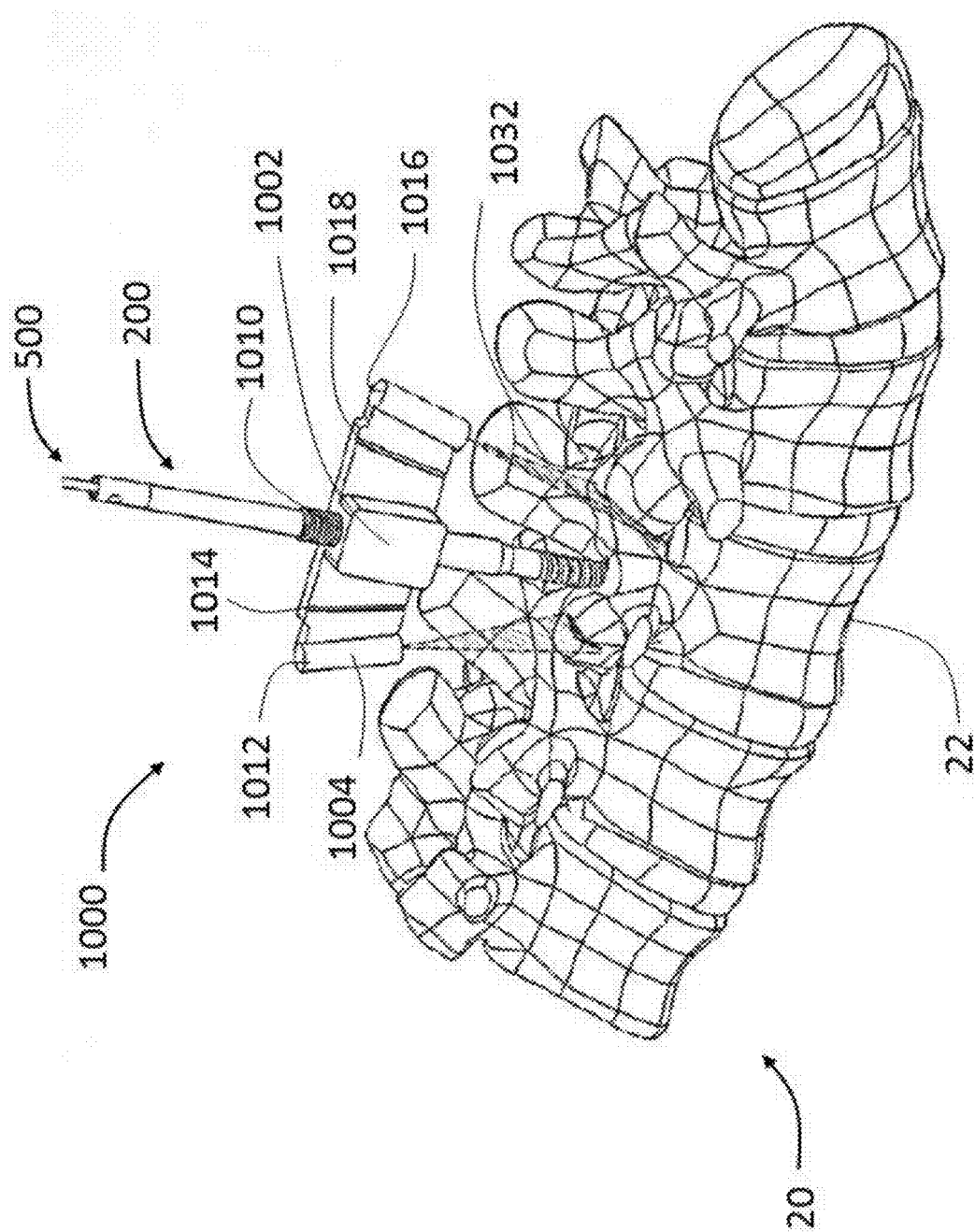
FIG. 21 is a perspective view of a cutting guide according to another embodiment of the present invention.
Figure 22:
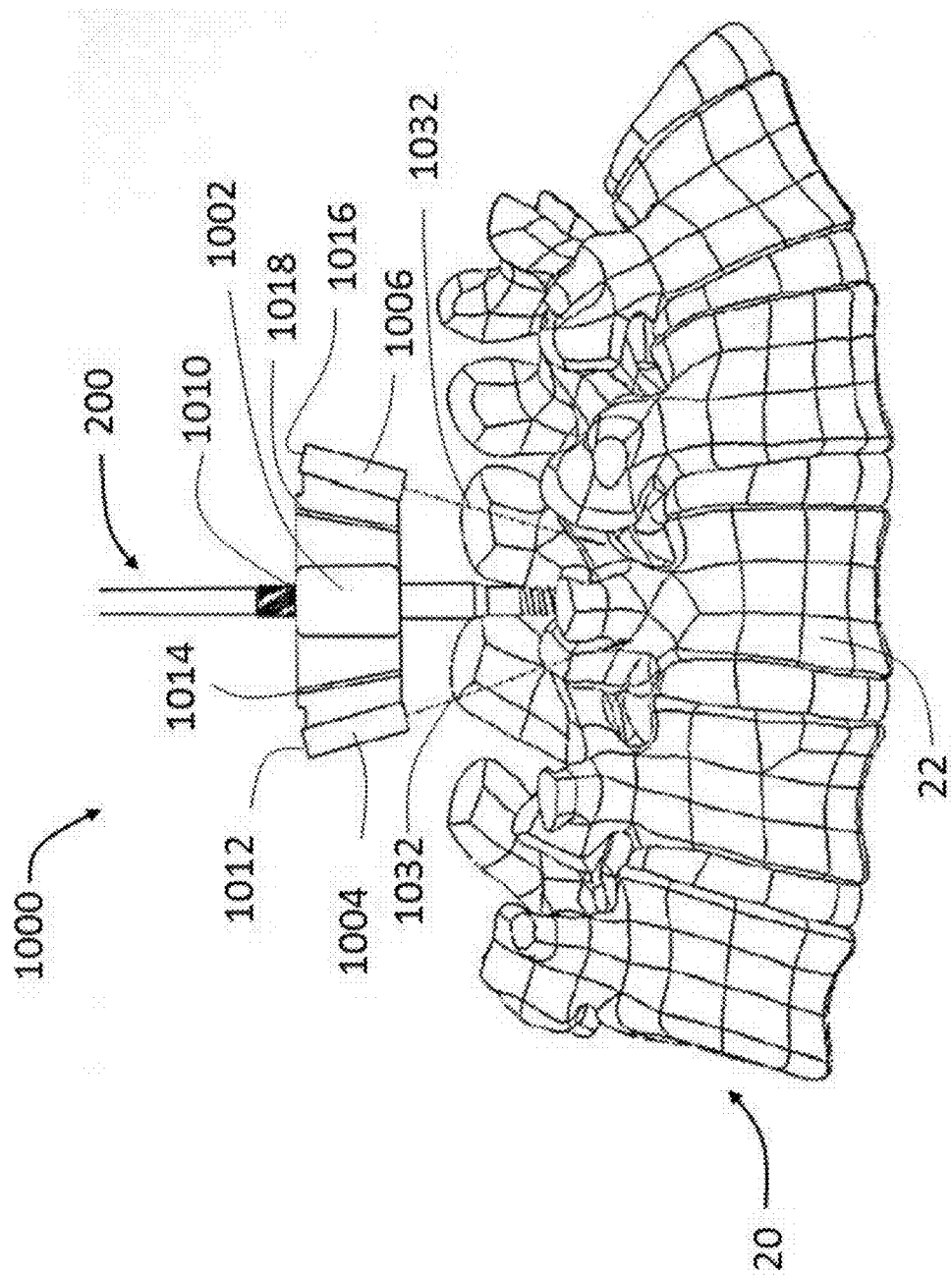
FIG. 22 is a front view of the cutting guide of FIG. 21.

FIGS. 21 and 22 show a cutting guide 1000 according to another embodiment of the present invention. Cutting guide 1000 is similar to cutting guide 900, and therefore like elements are referred to with similar numerals within the 1000-series of numbers. For instance, cutting guide 1000 includes superior reference marker 1014 and inferior reference marker 1018. Cutting guide 1000 includes a superior projector 1004 and an inferior projector 1016 capable of projecting a lighting source such as laser 1032 to indicate PSO cutting location and trajectory on vertebral body 22.

Figure 23B:
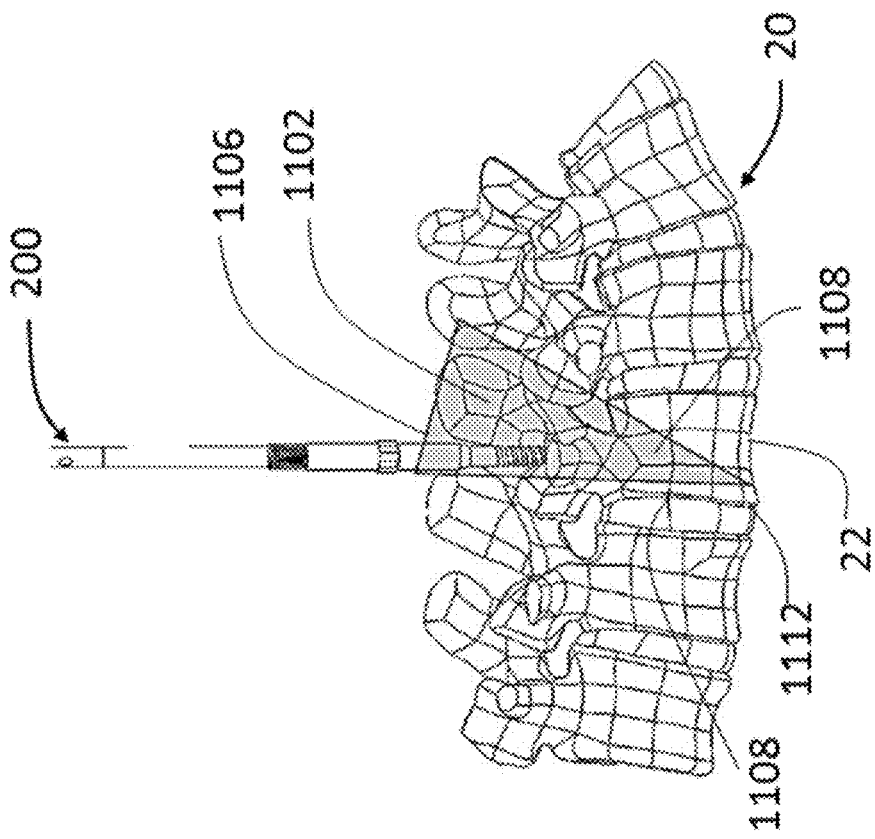
FIGS. 23A-23B are schematic front views of a projected cutting zone in conjunction with the post of FIG. 2 according to another embodiment of the present invention.
Figure 23A:
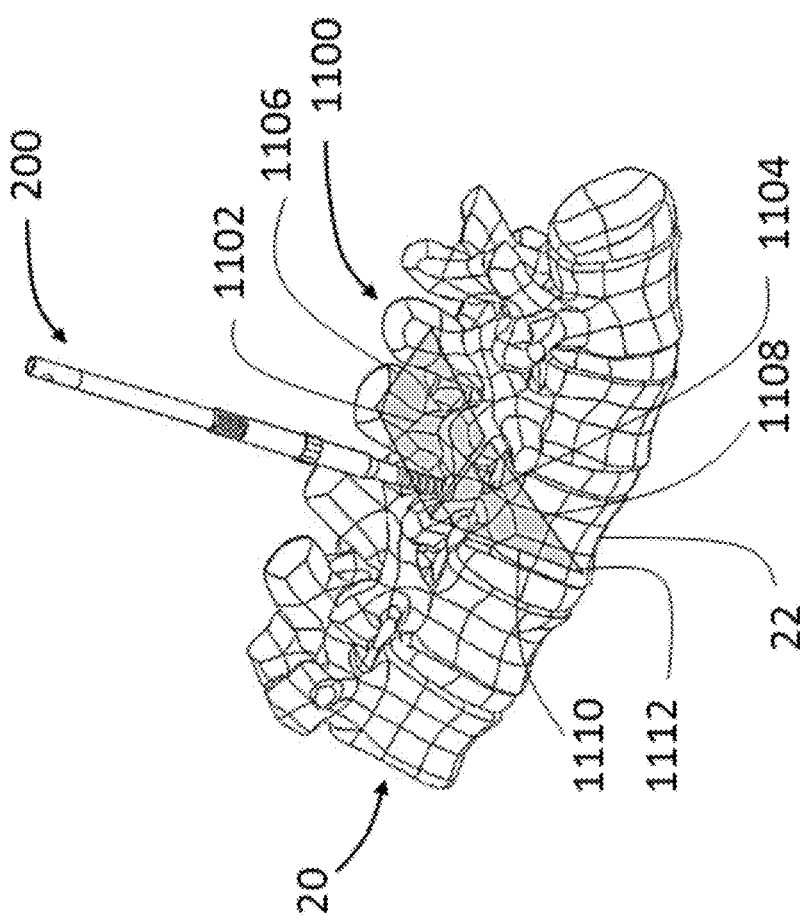

FIGS. 23A and 23 show a method for performing a PSO using post 200 in conjunction with a projected cutting zone 1100 according to another embodiment of the present invention. Projected cutting zone 1100 may be viewed either on a monitor or through augmented reality equipment (not shown) to aid a surgeon in placing and advancing cutting instruments. Projected cutting zone 1100 includes a coronal plane 1102 and a sagittal plane 1112 identifying the target cutting zone on vertebral body 22 of vertebra 20. Sagittal plane 1104 include an anterior line 1110 indicating the cutting depth and a resection angle line 1108 indicating the trajectory required to obtain a desired subtraction angle. A medial line 1106 on the coronal plane 1102 marks the location and trajectory of medial cutting instrument.

Figure 24:
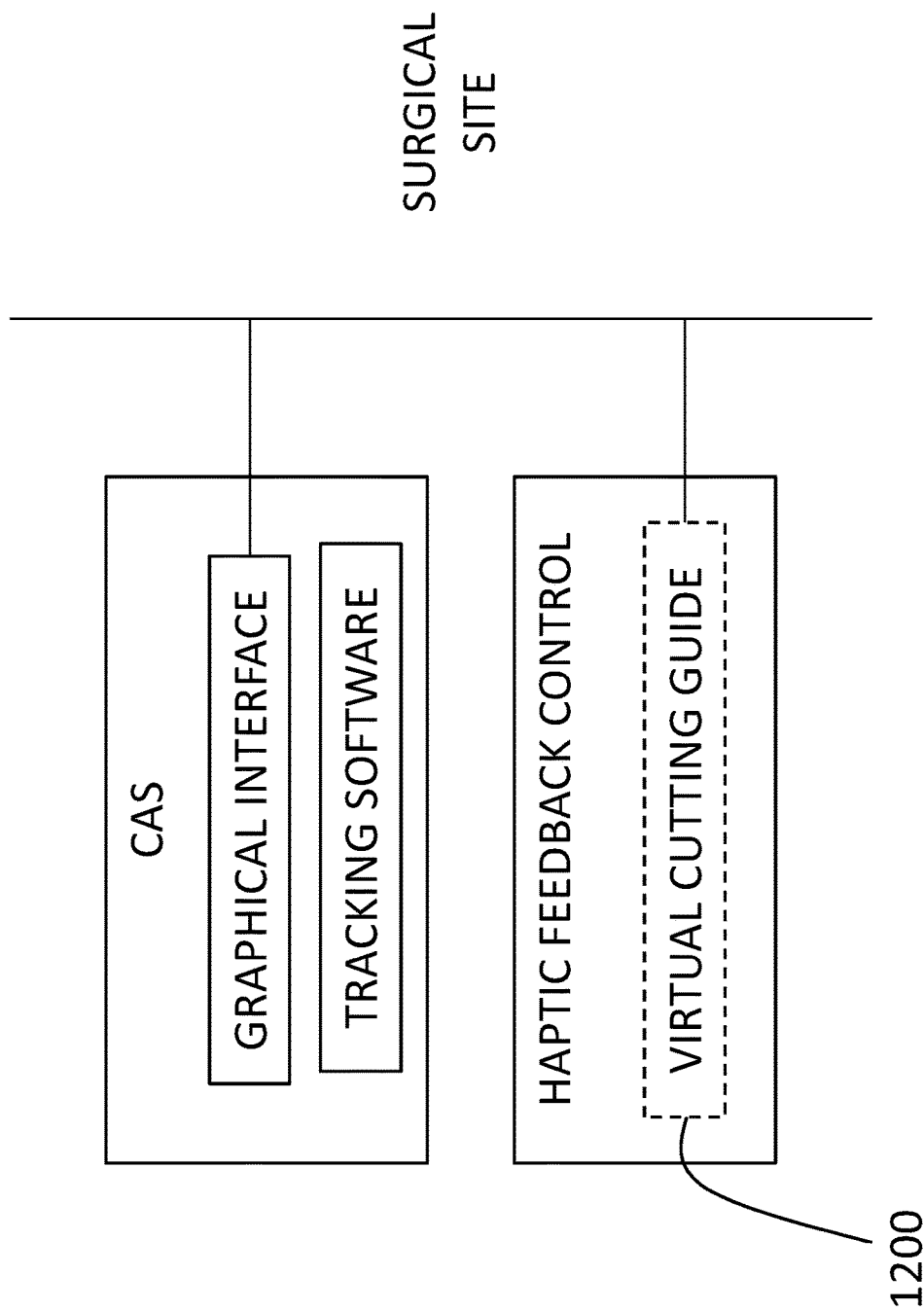
FIG. 24 is a schematic illustration of a computer-assisted surgery system with a haptic feedback control to perform a surgical procedure according to an embodiment of the present invention.

A haptic zone based on a virtual haptic geometry of the cutting guide of the present invention may also be used to perform various surgical cutting procedures as shown schematically in FIG. 24. A computer-assisted surgery ("CAS") system with surgical navigation, tracking software that displays a graphical representation of the surgical site, and haptic or force feedback controls may be coupled with cutting instruments. The virtual boundaries of the force feedback controls may be defined by the cutting guide to create a virtual cutting guide 1200. Using the graphical interface as a guide, a surgeon may manually navigate the cutting instruments within the virtual cutting guide boundary to perform the cutting procedure.

Cutting guides shown herein may be configured for specific areas of the spine. For example, cutting guides with greater height offsets from the vertebral body may be used for lumbar procedures to avoid crowding surgical instruments. Slots may be shaped to adapt for specific surgical tools such as rectangular slots for an oscillating saw, a round slot for a drill or a burr, and an arc-shaped slot for guiding a bur for a non-planar cut. Slot may be provided with bearings or bushing for easier guiding of the cutting instrument across or through the cutting guides. Robot-assisted surgery may also be used in conjunction with the cutting guide of the present invention. For example, a robot may hold and position cutting guide to determine the cutting depth without requiring a post to secure the cutting guide. Although a PSO procedure is generally described herein, cutting guides and cutting assemblies of the present invention may be used in any surgical cutting procedures.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A virtual surgical cutting guide for a spinal procedure comprising:
   a computer-assisted surgery system to generate a graphical representation of a surgical site;
   a haptic feedback control configured to be coupled with first and second cutting instruments, wherein the haptic feedback control defines a virtual boundary of the virtual surgical cutting guide, the virtual boundary comprising:

a first slot extending from a proximal face to a distal face, the first slot having a first axis extending therethrough and defining a first channel to receive the first cutting instrument, a second slot extending from the proximal face to the distal face, the second slot having a second axis therethrough, being located opposite the first slot and defining a second channel to receive the second cutting instrument, wherein when the virtual surgical cutting guide is positioned away from a vertebral body such that the distal face is facing the vertebral body, the first and second channels are oriented such that the first and second axes extend distally towards each other and intersect at a distal point located in an interior of the vertebral body, wherein an operator can manually navigate the first and second cutting instruments placed within the first and second channels of the virtual surgical cutting guide.

2. The virtual surgical cutting guide of claim 1, wherein the haptic feedback control includes force feedback to the first and second cutting instruments.

3. The virtual surgical cutting guide of claim 1, wherein the graphical representation of the site includes representations of the first and second cutting instruments.

4. The virtual surgical cutting guide of claim 1, wherein a cross-section of the first slot is substantially the same as a cross-section of the first cutting instrument and a cross-section of the second slot is substantially the same as a cross-section of the second cutting instrument such that haptic feedback control is configured to guide the first and second cutting instruments.

5. The virtual surgical cutting guide of claim 1, wherein the first slot and second slot have at least one or more similarly oriented slots respectively.

6. The virtual surgical cutting guide of claim 1, further including a third slot extending from the proximal face to the distal face of the virtual surgical cutting guide, the third slot being located between the first and second slots, the third slot being substantially transverse to the first and second slots and defining a third channel to receive a third cutting instrument, the third cutting instrument being coupled to the haptic feedback control.

7. The virtual surgical cutting guide of claim 6, wherein a cross-section of the third slot is substantially the same as a cross-section of the third cutting instrument such that haptic feedback control is configured to guide the third cutting instrument.

8. The virtual surgical cutting guide of claim 1, wherein a superior face of the cutting guide is parallel to the first channel and an inferior face of the cutting guide is parallel to the second channel.

9. The virtual surgical cutting guide of claim 8, wherein the superior face has peripheral ridges on medial and lateral edges to guide the first cutting tool, and the inferior face has peripheral ridges on medial and lateral edges to guide the second cutting tool.

10. The virtual surgical cutting guide of claim 1, wherein the intersection of the first and second axes defines a subtraction angle for a pedicle subtraction osteotomy.

11. A surgical cutting assembly for a spinal procedure comprising:
the virtual surgical cutting guide of claim 1,
a first cutting instrument having a cross-section that is substantially the same as the cross-section of the first channel such that the first cutting instrument can be disposed in the first channel and guided along the first axis; and a second cutting instrument having a cross-section that is substantially the same as a cross-section of the second channel such that the second cutting instrument can be disposed in the second channel and guided along the second axis.

12. The surgical cutting assembly of claim 11, wherein the first and second cutting instruments have first and second stoppers, respectively to limit distal movements of the first and second cutting instruments with respect to the virtual surgical cutting guide.

13. The surgical cutting assembly of claim 12, wherein the first and second cutting instruments each have distal cutting edges configured to contact each other at the distal point when the first and second cutting instruments are received in the first and second channels.

14. The surgical cutting assembly of claim 13, wherein the virtual surgical cutting guide further defines an opening extending from the proximal face to the distal face of the surgical cutting guide defining a third axis extending therethrough, the third axis intersecting with the first and second axes at the distal point.

15. A virtual surgical system for a spinal procedure comprising:
a computer-assisted surgery system to generate a graphical representation of a surgical site;
a haptic feedback control configured to be coupled with first and second cutting instruments, and
a virtual surgical cutting guide defining a virtual boundary for the haptic feedback control, the virtual surgical cutting guide comprising:
a first virtual boundary extending from a virtual proximal face to a virtual distal face, the first virtual boundary having a first axis extending therethrough and defining a first virtual channel to receive the first cutting instrument,
a second virtual boundary extending from the virtual proximal face to the virtual distal face, the second virtual boundary having a second axis therethrough, the second virtual boundary being located opposite the first virtual boundary and defining a second virtual channel to receive the second cutting instrument, wherein when the virtual surgical cutting guide is positioned away from a vertebral body such that the distal face is facing the vertebral body, the first and second virtual channels are oriented such that the first and second axes extend distally towards each other and intersect at a distal point located in an interior of the vertebral body,
wherein an operator can manually navigate the first and second cutting instruments and the virtual surgical cutting guide prevents movement of the first and second cutting instruments outside of the first and second virtual boundaries.

16. The virtual surgical cutting guide of claim 15, wherein the haptic feedback control includes force feedback to the first and second cutting instruments.

17. The virtual surgical cutting guide of claim 15, wherein the graphical representation of the site includes representations of the first and second cutting instruments.

18. The virtual surgical cutting guide of claim 15, wherein a cross-section of the first virtual channel is substantially the same as a cross-section of the first cutting instrument and a cross-section of the second virtual channel is substantially the same as a cross-section of the second cutting instrument such that haptic feedback control is configured to guide the first and second cutting instruments.

19. The virtual surgical cutting guide of claim 15, further including a third slot extending from the proximal face to the distal face of the virtual surgical cutting guide, the third slot being located between the first and second slots, the third slot being substantially transverse to the first and second slots and defining a third channel to receive a third cutting instrument, the third cutting instrument being coupled to the haptic feedback control.

20. The virtual surgical cutting guide of claim 19, wherein a cross-section of the third slot is substantially the same as a cross-section of the third cutting instrument such that haptic feedback control is configured to guide the third cutting instrument.

\* \* \* \* \*